United States Patent
Bader

(10) Patent No.: US 7,943,655 B2
(45) Date of Patent: May 17, 2011

(54) POLYMORPHIC AND PSEUDOPOLYMORPHIC FORMS OF TRANDOLAPRILAT, PHARMACEUTICAL COMPOSITIONS AND METHODS FOR PRODUCTION AND USE

(75) Inventor: Thomas Bader, Zürich (CH)

(73) Assignee: Universitat Zurich, Zurich (CH)

( * ) Notice: Subject to any disclaimer, the term of this patent is extended or adjusted under 35 U.S.C. 154(b) by 449 days.

(21) Appl. No.: 11/731,663

(22) Filed: Mar. 30, 2007

(65) Prior Publication Data

US 2007/0237817 A1    Oct. 11, 2007

Related U.S. Application Data

(60) Provisional application No. 60/789,806, filed on Apr. 5, 2006.

(51) Int. Cl.
*A61K 31/404* (2006.01)
*C07D 209/42* (2006.01)

(52) U.S. Cl. ........................ 514/412; 548/452
(58) Field of Classification Search .............. 424/464; 514/410, 412, 419; 548/452, 492
See application file for complete search history.

(56) References Cited

U.S. PATENT DOCUMENTS

| | | | |
|---|---|---|---|
| 4,743,450 A | 5/1988 | Harris et al. | 424/440 |
| 4,933,361 A | 6/1990 | Urbach et al. | 514/419 |
| 5,101,039 A | 3/1992 | Urbach et al. | 548/452 |
| 6,303,141 B1 | 10/2001 | Fischer et al. | 424/449 |
| 2004/0052835 A1 | 3/2004 | Klokkers et al. | 424/449 |
| 2004/0137054 A1 | 7/2004 | Hager et al. | 424/465 |

FOREIGN PATENT DOCUMENTS

| | | |
|---|---|---|
| EP | 0084164 | 12/1982 |
| WO | WO 2005/051909 A1 | 6/2005 |

OTHER PUBLICATIONS

Byrn et al., Solid-State Chemistry of Drugs, 1999, SSCI, Inc., Second Edition, pp. 62-63.*
Newman et al., Solid-state analysis of the active pharmaceutical ingredient in drug products, DDT, vol. 8, No. 19, Oct. 2003, pp. 898-905.*
Chawla et al., Challenges in Polymorphism of Pharmaceuticals, CRIPS, vol. 5, No. 1, Jan.-Mar. 2004, pp. 9-12.*
Brittain, Polymorphism in Pharmaceutical Solids, 1999, vol. 95, Marcel Dekker, Chapter 6, p. 228-229.*
C. J. Blankley et al., "Synthesis and Structure-Activity Relationships of Potent New Angiotensin Converting Enzyme Inhibitors Containing Saturated Bicyclic Amino Acids," J. Med. Chem. 30, 992-998 (1987).

* cited by examiner

*Primary Examiner* — Kamal A Saeed
*Assistant Examiner* — Kristin Bianchi
(74) *Attorney, Agent, or Firm* — Roberta L. Hastreiter; Scott B. Feder; Locke, Lord, Bissell & Liddell LLP

(57) ABSTRACT

The present invention provides novel polymorphic and pseudopolymorphic forms of Trandolaprilat, including crystalline Trandolaprilat Form A, crystalline Trandolaprilat Form B, crystalline Trandolaprilat Form C, crystalline Trandolaprilat Form D, crystalline Trandolaprilat Form E, and mixtures thereof. The invention also provides novel methods for producing Trandolaprilat, pharmaceutically acceptable salts of Trandolaprilat, and polymorphic and pseudopolymorphic forms of Trandolaprilat, pharmaceutical compositions including one or more novel Trandolaprilat compounds and methods for treating high blood pressure and/or cardiac insufficiency using one or more novel Trandolaprilat compounds.

41 Claims, 17 Drawing Sheets

Investigation of the transformation of Trandolaprilat crystalline Form B to Form E obtained according to investigation example 7; see example 5

Preparation of Trandolaprilat crystalline Form A according to the first process Methods for preparation of Trandolaprilat crystalline Forms B, C, D and E according to the second process

POLYMORPHIC AND PSEUDOPOLYMORPHIC FORMS OF TRANDOLAPRILAT, PHARMACEUTICAL COMPOSITIONS AND METHODS FOR PRODUCTION AND USE

This application is a non-provisional patent application that is being filed from, and claims the benefit of, prior pending Provisional Patent Application U.S. Ser. No. 60/789,806, filed on Apr. 5, 2006. Provisional Patent Application U.S. Ser. No. 60/789,806 is hereby incorporated into this non-provisional patent application in its entirety by reference.

BACKGROUND OF THE INVENTION

1. Field of the Invention

The present invention relates to novel polymorphic and pseudopolymorphic forms of Trandolaprilat, and mixtures thereof, novel methods for producing Trandolaprilat, pharmaceutically acceptable salts of Trandolaprilat, and polymorphic and pseudopolymorphic forms of Trandolaprilat, pharmaceutical compositions including one or more novel Trandolaprilat compounds and methods for treating high blood pressure and/or cardiac insufficiency using one or more novel Trandolaprilat compounds.

2. Background and Related Art

Trandolaprilat {(2S,3aR,7aS)-1-[[(2S)-2-[[(1S)-1-carboxy-3-phenylpropyl]amino]-propanoyl]octahydro-1H-indole-2-carboxylic acid} is an active metabolite of Trandolapril. Trandolapril and Trandolaprilat have the chemical structures that are shown below, respectively, and are both inhibitors of an enzyme known as the Angiotensin Converting Enzyme ("ACE enzyme"). The ACE enzyme is a peptidyl dipeptidase that catalyzes the conversion of angiotensin I to angiotensin II, which is a potent peripheral vasoconstrictor that also stimulates secretion of aldosterone by the adrenal cortex and provides negative feedback for renin secretion.

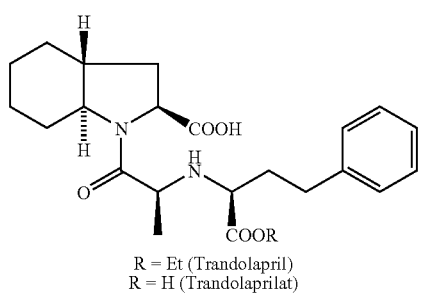

R = Et (Trandolapril)
R = H (Trandolaprilat)

As ACE inhibitors, Trandolapril and Trandolaprilat inhibit ACE activity, which results in an antihypertensive effect. Thus, Trandolapril and Trandolaprilat may be used to lower high blood pressure and to treat cardiac insufficiency and other medical conditions relating to hypertension. Their effect in hypertension appears to result primarily from the inhibition of circulating and tissue ACE activity, thereby reducing angiotensin II formation, decreasing vasoconstriction, decreasing aldosterone secretion and increasing plasma renin.

Trandolapril is the ethyl ester prodrug of Trandolaprilat, which is a nonsulfhydryl angiotensin converting enzyme (ACE) inhibitor. Trandolapril is deesterified to the diacid metabolite, Trandolaprilat. Trandolaprilat is described in the literature as being about eight times more potent than Trandolapril as an inhibitor of ACE activity. While Trandolapril may be administered as oral dosage forms, such as tablets or capsules, there is a transdermal administration using the ACE inhibitor in the form of dicarboxylic acid (e.g. Trandolaprilat), or as a therapeutically active salt, described in published patent application U.S. 2004/0052835 and U.S. Pat. No. 6,303,141.

As is described in published patent application US 2004/0052835, the use of certain non-stabilized ACE inhibitors in a transdermal patch caused problems because of a decomposition of the active ingredients employed in the patch. Such decomposition occurred within a short period of storage time, whereupon the limit for degradation products exceeded the tolerance. It is described in this document that the salts of the active metabolites (=dicarboxylic acids) of ACE inhibitors, which are formed by reaction of the dicarboxylic acids with strong acids (1:1) or bases (1:2), are substantially stable with respect to decomposition.

It is well known that, very disadvantageously, both Trandolapril and Trandolaprilat (unstabilized) have a tendency to decompose in decomposition reactions that occur during their synthesis and/or storage (cyclization to the corresponding diketopiperazine, as is shown below).

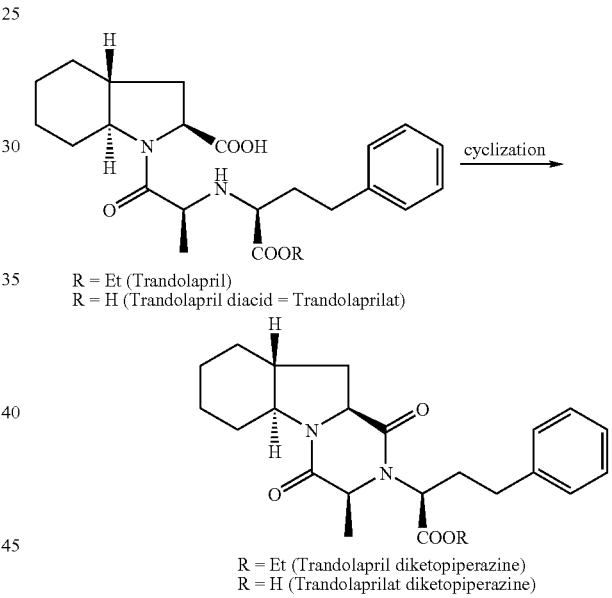

R = Et (Trandolapril)
R = H (Trandolapril diacid = Trandolaprilat)

R = Et (Trandolapril diketopiperazine)
R = H (Trandolaprilat diketopiperazine)

Trandolaprilat tends to decompose during its synthesis and isolation, which contaminates the end product and results in loss of yields.

Different methods and ingredients have been developed for the stabilization of Trandolapril and Trandolaprilat, particularly for the formulation of these compounds. See, for example, U.S. Pat. No. 4,743,450 or published patent application number U.S. 2004/0137054.

The aforementioned problems show that there is an ongoing need to develop new, robust and efficient methods for the preparation and stabilization of ACE inhibitors, which tend to decompose. In addition, or alternatively, to the above-described methods, it has been determined that other such methods can include an investigation and evaluation of different crystalline forms of the ACE inhibitors because they can play a decisive role in the stability of the compounds.

In general, a compound can exist in different crystalline forms as well as in a non-crystalline form. Generally a non-crystalline solid is referred to as an "amorphous form," which consists of disordered arrangements of molecules. Different crystalline forms of the same compound arise from different packing of the molecules in the solid state, which results in different crystal symmetries and/or unit cell parameters. Such crystalline forms are referred to as "polymorphic forms" and/or "non-solvated forms," which means that they are essentially free of residual organic solvents. If the substances incorporate stoichiometric or non-stoichiometric amounts of water (hydrates), or any other solvent(s) (solvates), in the crystal structure, they are referred to as "pseudopolymorphic forms."

Many compounds are known to exist in various polymorphic, pseudopolymorphic or amorphous forms. Such different solid forms can have different physical, spectroscopic and/or chemical properties, such as solubilities and dissolution rates, melting points, densities, stabilities and flow properties. For active compounds, solubilities and dissolution rates may have an influence on their bioavailabilities, densities and flow properties, which have to be considered during formulation. Further, chemical and physical (thermodynamical) stabilities of these compounds are important, for example, with regard to decomposition or conversion of thermodynamically less stable (kinetically favored) polymorphs into more stable polymorphs, which can affect the biological activities of these compounds.

Methods for synthesizing Trandolapril are disclosed in, e.g., EP 0084164 (and its counter part U.S. Pat. No. 4,933,361) and in WO 2005/051909.

Methods for suitably preparing Trandolaprilat from Trandolapril are not described in the literature. Although a preparation of a diastereomeric isomer of Trandolaprilat is described in J. Med. Chem. 30, 992-998 (1987), for the isolation of the diacid, it was necessary to lyophilize the mixture produced, and to purify the resulting residue by ion-exchange chromatography on Amberlite IR-120. Disadvantageously, this method is not suitable for a large-scale production of Trandolaprilat.

An additional preparation of Trandolaprilat is described in U.S. Pat. No. 5,101,039. A specific procedure is not provided, and the procedure that is referred to suffers from several disadvantages: it does not provide crystalline material; it requires the removal of water under vacuum; and it relies on the use of di-isopropyl ether as solvent. Crystalline material is clearly more desirable in terms of isolation and purification; removal of water under vacuum is time consuming; and di-isopropyl ether is very prone to forming dangerous peroxides. Thus, this is not a suitable technical process.

In view of the above, it would be beneficial to provide efficient, reliable and robust processes for preparing Trandolaprilat, and salts, polymorphs, pseudopolymorphs and mixtures thereof, on a large scale, and polymorphs and pseudopolymorphs of Trandolaprilat that have an improved stability during synthesis and storage.

SUMMARY OF THE INVENTION

Advantageously, the present invention provides efficient, reliable and robust processes for preparing Trandolaprilat, and salts, polymorphs, pseudopolymorphs and mixtures thereof, on a large scale with high yields and purities, as well as different polymorphic and pseudopolymorphic forms of Trandolaprilat that have an improved stability (a decreased tendency to undergo cyclization to the corresponding diketopiperazine) during synthesis and storage in comparison with the non-solvate form of Trandolaprilat. It has been determined that the crystal form of the Trandolaprilat plays an important role in its stabilization, as well as allowing for its efficient, robust and pure preparation from Trandolapril.

Because unstabilized Trandolaprilat has a high tendency of decomposing, particularly by cyclization to the corresponding diketopiperazine derivative, the preparation and purification (e.g. recrystallization at higher temperatures) of the diacid are very difficult, and result in a loss of yield and, often, an unacceptably low purity.

It has been surprisingly and unexpectedly determined that the diacid of Trandolapril (Trandolaprilat) forms different pseudopolymorphic forms with alcohols and/or water, which different pseudopolymorphic forms have an increased stability during synthesis and/or storage compared with the non-solvate form of Trandolaprilat (especially with respect to cyclization to the corresponding diketopiperazine), and can be prepared in high yields and purities. It was further determined that these pseudopolymorphic forms of Trandolaprilat can be transformed under mild conditions to the unstabilized (non-solvate) form in high yields and purities.

In one aspect, the present invention provides a process for preparing crystalline Trandolaprilat in a polymorphic or pseudopolymorphic form comprising the steps of:
(a) providing Trandolaprilat in its free amino acid form in a solution containing n-butanol and water; and
(b) removing a sufficient amount of water from the solution to induce crystallization of Trandolaprilat.

In another aspect, the present invention provides a process for preparing Trandolaprilat comprising the steps of:
(a) reacting Trandolapril with a hydroxide compound in a saponification reaction solvent at a temperature, and for a period of time, that is effective for permitting at least an almost complete saponification, wherein the hydroxide compound is an alkaline metal hydroxide, an alkaline-earth metal hydroxide, a tetraalkylammonium hydroxide or a substituted alkylammonium hydroxide, and wherein the Trandolapril, the hydroxide compound and the saponification reaction solvent are each employed in amounts that are effective for producing a reaction mixture that includes a salt of formula 3:

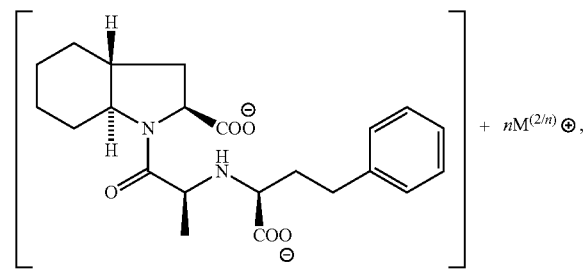

(3)

wherein M is an alkaline metal, an alkaline-earth metal, tetraalkylammonium or a substituted alkylammonium ion and n is 1 or 2;
(b) mixing the reaction mixture of step (a) with an amount of acid, for a period of time, and at a temperature, that are effective for causing the pH of the mixture to reach its isoelectric point and providing Trandolaprilat in its free amino acid form; and
(c) isolating Trandolaprilat in its free amino acid form from the reaction mixture resulting from step (b).

In a further aspect, the present invention provides a process for preparing crystalline Trandolaprilat in a polymorphic or pseudopolymorphic form comprising the steps of:
(a) reacting Trandolapril with a hydroxide compound in a saponification reaction solvent selected from water, C1-C4 alcohols and mixtures thereof at a temperature, and for a period of time, that is effective for permitting at least an almost complete saponification, wherein the hydroxide compound is an alkaline metal hydroxide, an alkaline-earth metal hydroxide, a tetraalkylammonium hydroxide or a substituted alkylammonium hydroxide, and wherein the Trandolapril, the hydroxide compound and the saponification reaction solvent are each employed in amounts that are effective for producing a reaction mixture that includes a salt of formula 3:

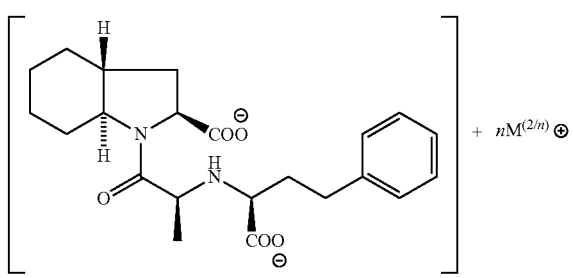

(3)

wherein M is an alkaline metal, an alkaline-earth metal, tetraalkylammonium or a substituted alkylammonium ion and n is 1 or 2;
(b) if the saponification reaction solvent employed in step (a) includes an alcohol other than n-butanol, removing such alcohol from the reaction mixture of step (a);
(c) if the reaction mixture of step (b) is not an aqueous solution, adding an amount of water to the reaction mixture that is effective for providing an aqueous solution;
(d) mixing the product of step (c) with an amount of acid, for a period of time, and at a temperature, that are effective for causing the pH of the mixture to reach its isoelectric point and providing Trandolaprilat in its free amino acid form;
(e) extracting Trandolaprilat from the mixture of step (d) with an amount of n-butanol, and at a temperature, that are effective for providing Trandolaprilat in its free amino acid form in a solution containing n-butanol and water; and
(f) removing an amount of water from the solution of step (e) that is sufficient to induce crystallization of the Trandolaprilat and provide crystalline Trandolaprilat in a polymorphic or pseudopolymorphic form.

In yet another aspect, the present invention provides a process for producing Trandolaprilat in a substantially pure crystalline form, or as a mixture of different crystalline forms, comprising the steps of:
(a) reacting Trandolapril with a hydroxide compound in a saponification reaction solvent selected from water, C1-C4 alcohols and mixtures thereof at a temperature, and for a period of time, that is effective for permitting at least an almost complete saponification, wherein the hydroxide compound is an alkaline metal hydroxide, an alkaline-earth metal hydroxide, a tetraalkylammonium hydroxide or a substituted alkylammonium hydroxide, and wherein the Trandolapril, the hydroxide compound and the saponification reaction solvent are each employed in amounts that are effective for producing a reaction mixture that includes a salt of formula 3:

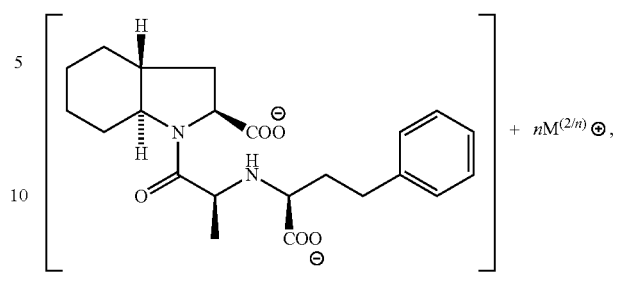

(3)

wherein M is an alkaline metal, an alkaline-earth metal, tetraalkylammonium or a substituted alkylammonium ion and n is 1 or 2, and wherein, if the saponification reaction solvent comprises a mixture of a C1-C4 alcohol and water, the C1-C4 alcohol and water are present in a ratio that is effective for permitting at least an almost complete saponification;
(b) if the saponification reaction solvent employed in step (a) includes a C4 alcohol, removing the C4 alcohol from the reaction mixture of step (a);
(c) if the reaction mixture of step (b) is not an aqueous solution, adding an amount of water to the reaction mixture that is effective for providing an aqueous solution;
(d) mixing the product of step (c) with an amount of an acid, and for a period of time, and at a temperature, that are effective for causing the pH of the mixture to reach its isoelectric point and providing Trandolaprilat in a substantially pure free amino acid form, or as a mixture of at least two different free amino acid forms;
(e) separating the product of step (d) from the supernatant; and
(f) drying the product of step (e) to provide Trandolaprilat in a substantially pure crystalline form, or as a mixture of at least two different crystalline forms.

In another aspect, the present invention provides a process for producing Trandolaprilat in a substantially pure crystalline form, or as a mixture of crystalline forms, comprising the steps of:
(a) reacting Trandolapril with at least 2.0 equivalents of NaOH in a saponification reaction solvent including ethanol and water in a ratio of from about 1/1 to about 1/1.5 by volume at a temperature ranging from about 20° C. to about 25° C. for a period of time that is sufficient for producing a reaction mixture that includes a salt of formula 3:

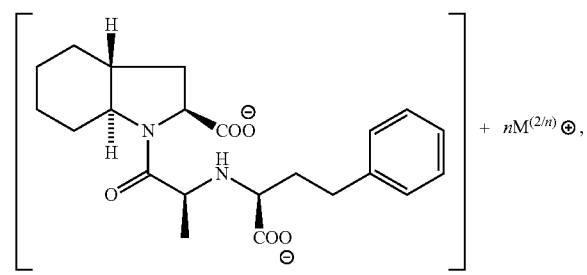

(3)

wherein M is sodium and n is 2;
(b) adjusting the pH of the product of step (a) with hydrochloric acid to a range from about 3.6 to about 4.0 to provide Trandolaprilat in a substantially pure free amino acid form, or as a mixture of at least two different free amino acid forms;

(c) separating the product of step (b) from the supernatant; and (d) drying the product of step (c) to provide Trandolaprilat in a substantially pure crystalline form, or as a mixture of at least two different crystalline forms.

In another aspect, the present invention provides Trandolaprilat in a crystalline form comprising a structure of formula 4:

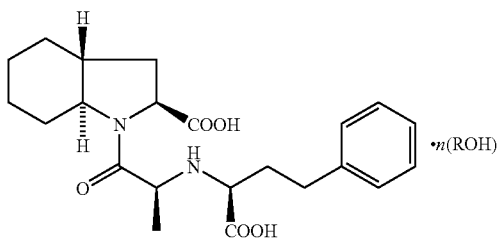

(4)

wherein R is H or a C1-C4 alkyl and n ranges from 0 to 2, and may be stoichiometric or non-stoichiometric.

In another aspect, the present invention provides crystalline Trandolapril which is Trandolaprilat Form A, Trandolaprilat Form B, Trandolaprilat Form C, Trandolaprilat Form D or Trandolaprilat Form E, pharmaceutical compositions comprising an pharmaceutically effective amount of crystalline Trandolaprilat Form A, B, C, D and/or E, and methods of treatment comprising administering one or more of Trandolaprilat Forms A, B, C, D and/or E pharmaceutical composition comprising at least one crystalline Trandolaprilat selected from the group consisting of Trandolaprilat Form A, Trandolaprilat Form B, Trandolaprilat Form C, Trandolaprilat Form D and Trandolaprilat Form E.

DETAILED DESCRIPTION OF THE PREFERRED EMBODIMENTS

Figure 1:
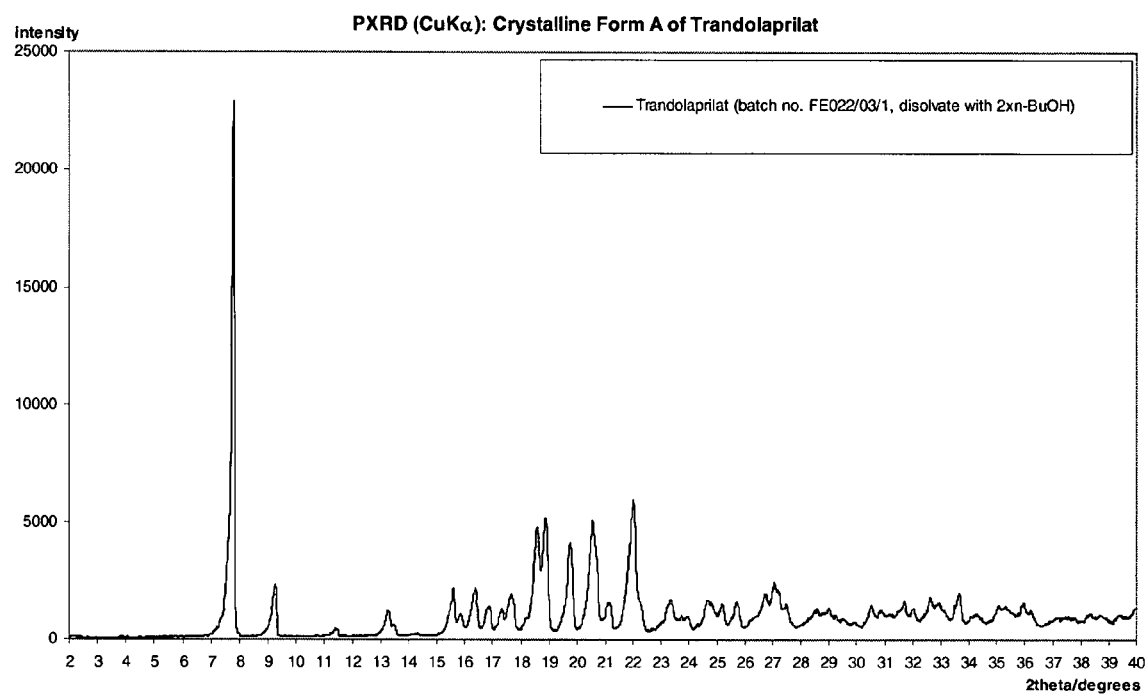
FIG. 1 is an X-ray powder diffraction pattern of crystalline Trandolaprilat Form A.

The present invention may be understood more readily by reference to the following detailed description of the preferred embodiments of the invention, and to the examples included therein.

Definitions

For purposes of clarity, various terms and phrases used throughout this specification and the appended claims are defined in the manner set forth below. If a term or phrase used in this specification, or in the appended claims, is not defined below, or otherwise in this specification, the term or phrase should be given its ordinary meaning.

The phrase "administered transdermally" as used herein means an application onto the skin (generally onto one or more exposed or outer surfaces thereof, such as the epidermis), for example, using hands, fingers or a wide variety of applicators (spray, pump, brush, mat, powder puff, cotton ball, cue tip, patch and the like). The application may be made, for example, by laying, pouring, spreading, spraying, sprinkling or massaging into, or onto, the skin or hair, or by any other convenient or suitable method.

The phrase "amorphous form" as used herein in connection with a compound means a compound that is a non-crystalline solid (i.e., not in a crystalline form), which consists of disordered arrangements of molecules.

The phrase "cardiac insufficiency" as used herein means an inadequate blood flow to the heart muscles, which can cause angina pectoris.

The term "crystal" as used herein means a solid formed by a solidification of a chemical compound that generally has a regular atomic structure (characteristic shapes and cleavage planes formed by the arrangement of its atoms, ions or molecules, which generally comprises a definite pattern called a "lattice").

The term "crystallization" as used herein means the formation of crystals.

The term "cyclization" as used herein means a formation of a ring or ring compound from a chain by a formation of a new bond.

The phrase "effective amount" as used herein in connection with a compound or pharmaceutical composition discussed herein means an amount of the compound or pharmaceutical composition that is effective to provide, or enhance, a cardiac or other health and/or medical benefit to a subject, such as a human being. Using the information that is provided herein, and information that is known, those of ordinary skill in the art can readily determine an amount of one or more of the compounds and pharmaceutical compositions discussed herein that would be effective for providing, or enhancing, a cardiac, health and/or medical benefit to a human and a wide variety of animals under a wide variety of different medical situations.

The abbreviation "Et" as used herein means ethyl.

The term "hydrate" as used herein means a crystalline form of a compound that incorporates a stoichiometric or non-stoichiometric amount of water in the crystal structure.

The abbreviation "n.d." as used herein, such as in Table 7, means not determined.

The abbreviation "PXRD" as used herein means powder X-ray diffraction.

The phrase "pharmaceutically acceptable" as used herein refers to those compounds, materials, compositions and/or dosage forms that are, within the scope of sound medical judgment, suitable for use in contact with the tissues of human beings and/or animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a solid or liquid filler, diluent, excipient, solvent or encapsulating material, that is involved in carrying or transporting a chemical compound or pharmaceutical agent from one organ, tissue or portion of the body to another organ, tissue or portion of the body. Examples of materials that can serve as pharmaceutically-acceptable carriers include, but are not limited to, sugars, such as lactose, glucose and sucrose, starches, such as cornstarch and potato starch, cellulose and its derivatives, gelatin, waxes, oils, water, and other substances that are known by those of skill in the art to be employed in pharmaceutical formulations.

The phrase "pharmaceutically acceptable salts" as used herein refers to non-toxic salts of the Trandolaprilat compounds of the present invention, which may generally be prepared by reacting a free base with a suitable organic or inorganic acid, or reacting a free acid with a suitable base. Those of skill in the art may readily determine which acids and/or bases are suitable for producing a pharmaceutically acceptable salt of a Trandolaprilat compound.

The phrases "polymorph," "polymorphic form" and "non-solvated form" as used herein refer to a crystalline form of a compound (a compound that has its molecules packed in a solid state in a particular crystal symmetry and/or unit cell parameter) that is essentially free of (i.e., less than about 2%): (a) water; and (b) other residual and/or non-residual organic or other solvents in the crystalline material.

The phrases "pseudopolymorph" and "pseudopolymorphic form" as used herein refer to a crystalline form of a compound (a compound that has its molecules packed in a solid state in a particular crystal symmetry and/or unit cell parameter) that incorporates in its crystal structure: (a) a stoichiometric or non-stoichiometric amount of water (hydrates); or (b) an amount of one or more other solvents (solvates).

The term "saponification" as used herein means the hydrolysis of an ester under basic conditions to form an alcohol and the salt of the acid.

The term "seeding" as used herein means starting or promoting a crystallization event using a small amount of material.

The term "solvate" as used herein means a crystalline form of a compound that incorporates an amount of one or more solvents in the crystal structure.

The phrase "straight or branched chain C1-C4 alcohols" as used herein includes, for example, methanol, ethanol, n-propanol, 2-propanol, n-butanol, 2-butanol, isobutyl alcohol and t-butanol.

The term "subject" as used herein includes human beings and animals.

The phrase "substantially pure" as used herein in connection with a form of crystalline Trandolaprilat means that the crystalline Trandolaprilat contains at least about 70% of one crystalline form of Trandolaprilat, and preferably contains at least about 80% of one crystalline form of Trandolaprilat, and more preferably contains at least about 90% of one crystalline form of Trandolaprilat, and most preferably contains at least about 95% of one crystalline form of Trandolaprilat.

The abbreviation "XRPD" as used herein means X-ray powder diffraction.

General Description

Because Trandolaprilat (unstabilized) tends to decompose during its synthesis and isolation, which disadvantageously results in a contamination of the end product and loss of yields, it was desired to find a simple, efficient and robust process that permits a preparation of Trandolaprilat in substantially pure form and in high yields that avoids difficulties that exist with respect to other scaleable methods, such as isolation of the compound by lyophilization and purification by using ion exchanger, as is described for the Trandolaprilat diastereomer in J. Med. Chem. 30, 992-998 (1987).

Efficient, reliable and robust processes for preparing and isolating Trandolaprilat, and salts, polymorphs, pseudopolymorphs and mixtures thereof, on a large scale have been developed that preferably avoid lyophilization, and purification of the product using an ion exchanger. The novel processes can be used for the scaleable synthesis of Trandolaprilat in high yields and purities.

Additionally, new methods for stabilizing Trandolaprilat by formation of novel, stable crystalline forms that have advantageously been discovered. These novel crystalline forms of Trandolaprilat have an improved stability (a decreased tendency to undergo cyclization to the corresponding diketopiperazine) during synthesis and storage in comparison with the non-solvate (unstabilized) form of Trandolaprilat.

Preferred among the novel polymorphic and pseudopolymorphic forms of Trandolaprilat that can be produced according to the methods of the present invention are Trandolaprilat crystalline Form A, Trandolaprilat crystalline Form B, Trandolaprilat crystalline Form C, Trandolaprilat crystalline Form D and Trandolaprilat crystalline Form E, and various mixtures thereof. Important characteristics of these forms of Trandolaprilat, as well as procedures and examples for preparing them, are summarized below. The "First Procedure" and "Second Procedure" correspond with two different synthesis procedures that are described in detail hereinbelow. The example numbers correlate with the examples that are present in the Examples section set forth hereinbelow.

| | | Trandolaprilat Forms A-E | |
|---|---|---|---|
| Form | Procedure used to Produce | Polymorphic or Pseudopolymorphic | Characteristics |
| Form A | First Procedure (crystallization from n-butanol/water) Example 1 | Pseudopolymorphic | Contains 2 equivalents of n-butanol bound in its crystalline structure (a disolvate with n-butanol) |

-continued

| Form | Procedure used to Produce | Polymorphic or Pseudopolymorphic | Characteristics |
|---|---|---|---|
| Form B | Second Procedure (crystallization/slurry from ethanol or ethanol/water) Example 2, Example 5 (Investigation Examples 1 and 5) | Pseudopolymorphic | Contains 2 equivalents of ethanol bound in its crystalline structure (a disolvate with ethanol) |
| Form C | Second Procedure (crystallization from water) Example 3 | Pseudopolymorphic | Contains a non-stoichiometric amount of water (an amount ranging from about 5.4% to about 6.4%) bound in its crystalline structure |
| Form D | Second Procedure (crystallization from water) Example 4 | Pseudopolymorphic | Contains 1 equivalent of water bound in its crystalline structure (monohydrate), which is a stoichiometric amount of water (an amount ranging from about 4.1% to about 4.2%) |
| Form E | Second Procedure Example 5 (Investigation Examples 2, 3, 6, 7) Example 6 | Polymorphic | Produced from Form B with the ethanol removed by drying (a non-solvate) Has a water content of less than about 1.0% (non-solvate) and a content of residual solvent according to the limits described in the ICH Guideline |

Procedure for the Preparation and Isolation of Trandolaprilat

In one aspect, the present invention provides a novel process for the preparation and isolation of Trandolaprilat (1):

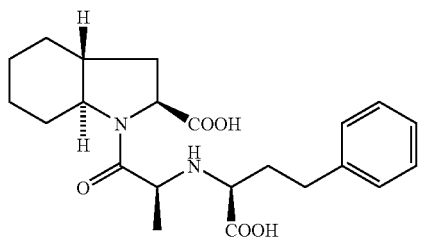

(1)

comprising the steps of:
(a) reacting Trandolapril (2):

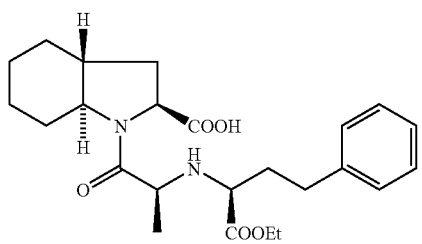

(2)

with a hydroxide compound in a saponification reaction solvent at a temperature, and for a period of time, that is effective for permitting at least an almost complete saponification, wherein the hydroxide compound is an alkaline metal hydroxide, an alkaline-earth metal hydroxide, a tetraalkylammonium hydroxide or a substituted alkylammonium hydroxide, and wherein the Trandolapril, the hydroxide compound and the saponification reaction solvent are each employed in amounts that are effective for producing a reaction mixture that includes a salt of formula (3):

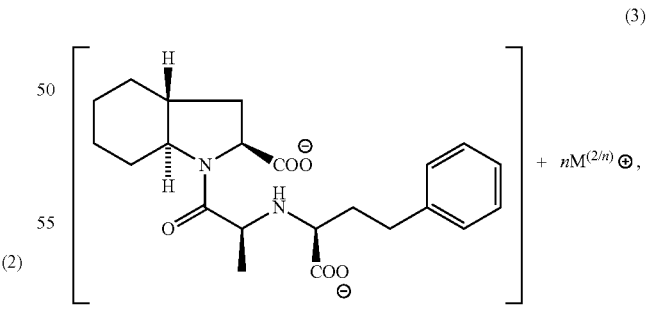

(3)

wherein M is an alkaline metal, an alkaline-earth metal, a tetraalkylammonium or a substituted alkylammonium ion and n is 1 or 2;

(b) mixing the reaction mixture of step (a) with an amount of acid, for a period of time, and at a temperature, that are effective for causing the pH of the mixture to reach its isoelectric point and providing Trandolaprilat in its free amino acid form; and (c) isolating Trandolaprilat in its free amino acid form from the reaction mixture resulting from step (b).

The steps of the above process are described in more detail below.

Step (a)

Hydroxide Compound

The hydroxide compound that is employed in step (a) is preferably an alkaline metal hydroxide, an alkaline-earth metal hydroxide, a tetraalkylammonium hydroxide or a substituted alkylammonium hydroxide. Examples of alkaline metal hydroxides that may be employed include sodium hydroxide (NaOH), potassium hydroxide (KOH), lithium hydroxide (LiOH) and the like. Examples of alkaline-earth metal hydroxides that may be employed include magnesium hydroxide, calcium hydroxide and the like. Examples of tetraalkylammonium hydroxides that may be employed preferably, include those in which the alkyl group ranges from tetrabutammonium hydroxide methyl to hexyl. Substituted alkylammonium hydroxides may also be employed, benzyl (trimethylammonium)hydroxide and the like. Preferred among the hydroxide compounds are the alkaline metal hydroxides, especially sodium hydroxide.

Saponification Reaction Solvent

The saponification reaction solvent that may be employed in step (a) includes: (i) straight or branched chain C1-C4 alcohols; (ii) water; and (iii) any mixture of (i) and/or (ii), for example, a mixture of ethanol and water. The saponification reaction solvent employed in step (a) preferably is ethanol, water or a mixture of ethanol and water, and most preferably is a mixture of ethanol and water.

When the saponification reaction solvent is a mixture of a C1-C4 alcohol, such as ethanol, and water, the ratio between the C1-C4 alcohol and water may have a wide range, preferably from about 5:1 to about 1:5 by volume, and more preferably from about 2:1 to about 1:2 by volume, and still more preferably from about 1.5:1 to about 1:1.5 by volume, with a ratio of about 1/1 by volume being most preferred.

Amounts of Reactants and Solvent

The Trandolapril, hydroxide compound and saponification reaction solvent that are employed in step (a) are each employed in amounts that are effective for producing a reaction mixture that includes a salt of formula (3), as is described hereinabove. Such amounts can readily be determined by those of ordinary skill in the art. However, preferably a range of from about 9 to about 14 percent Trandolapril (weight to volume).

In a preferred embodiment of this process, at least sufficient amounts of the hydroxide compound are employed that provide at least 2.0 equivalents of hydroxide in the reaction mixture. In another preferred embodiment, the hydroxide compound is provided in an amount that is in excess of the amount of Trandolapril employed, preferably in an amount of about 3.0 equivalents, more preferably in an amount of about 2.5 equivalents and most preferably in an amount of about 2.2 equivalents relative to the amount of Trandolapril employed.

Temperature

Step (a) is performed at a temperature that preferably is effective for permitting at least an almost complete saponification (e.g., about 80% or more of the Trandolapril is converted to Trandolaprilat), and more preferably for permitting a substantially complete saponification. The conversion may be monitored by methods known by those of ordinary skill in the art, such as high performance liquid chromatography ("HPLC"). This temperature generally ranges from about 0° C. to about 40° C., and preferably ranges from about 15° C. to about 25° C., may conveniently be carried out at room temperature. Higher temperatures may disadvantageously result in higher amounts of impurities being formed, which may be caused by an epimerization of the salt of formula (3) in the presence of excess hydroxide compound (base). Step (a) may be performed for a period of time (e.g., 12-20 hours) effective for permitting at least an almost complete saponification, e.g., 15 hours at 20-25° C.

Salt of Formula 3

In the salt of formula (3) that is formed in step (a), M may be an alkaline metal, an alkaline-earth metal, a tetraalkylammonium ion or a substituted alkylammonium ion as described hereinbefore.

Step (b)

Acid

In step (b), the reaction mixture of step (a) is mixed with an amount of acid that is effective for causing the pH of the mixture to reach its isoelectric point, and providing Trandolaprilat in its free amino acid form. Such a pH will generally range from about 3.6 to about 4.0. Such an amount of acid can readily be determined by those of ordinary skill in the art.

Acids that may be employed in step (b) for the acidification of the reaction mixture of step (a) to the isoelectric point include, for example, hydrochloric acid, hydrobromic acid, sulfuric acid, alkyl sulfonic acids, aryl sulfonic acids or phosphoric acid. Preferably, the acid employed is hydrochloric acid.

Temperature

In step (b), the mixing of the acid with the reaction mixture of step (a) preferably occurs at a temperature that is effective for causing the pH of the mixture to reach its isoelectric point, and providing Trandolaprilat in its free amino acid form without substantially degrading the Trandolaprilat.

Time

In step (b), the mixing of the acid with the reaction mixture of step (a) preferably occurs for a period of time that is effective for causing the pH of the mixture to reach its isoelectric point, and providing Trandolaprilat in its free amino acid form, such as, for example, from about 0.5 hours to about 48 hours, and preferably from about 0.5 hours to about 6 hours.

Step (c)

In step (c), Trandolaprilat in its free amino acid form is isolated from the mixture of step (b) by extraction or by precipitation. Methods for such isolation are described hereinbelow, and may be routinely determined by those of ordinary skill in the art.

Purity and Yield

The Trandolaprilat produced by this process is generally produced in a yield of at least about 80%, and is preferably produced in a yield of at least about 85%, and is more preferably produced in a yield of at least about 90%.

Further, the Trandolaprilat produced by this process is generally at least substantially pure, and preferably has a purity of at least about 85%, and more preferably has a purity of at least about 90%, and still more preferably has a purity of at least about 95%.

Procedure for The Preparation and Isolation of Crystalline Trandolaprilat in a Polymorphic or Pseudopolymorphic Form—(First Procedure)

In another aspect, the present invention provides a novel process for the preparation and isolation of crystalline Trandolaprilat in a polymorphic or pseudopolymorphic form, including crystalline Trandolaprilat Form A (a pseudopolymorph of Trandolaprilat).

It was surprisingly and unexpectedly found that Trandolaprilat as its free amino acid form is soluble in n-butanol saturated with water, and that this n-butanol/water mixture can be used for an extraction of Trandolaprilat with n-butanol from the water layer after adjusting the pH of the reaction mixture to the isoelectric point.

Thus, this aspect of the invention is a process for preparing crystalline Trandolaprilat in a polymorphic or pseudopolymorphic form comprising the steps of:

(a) reacting Trandolapril (2):

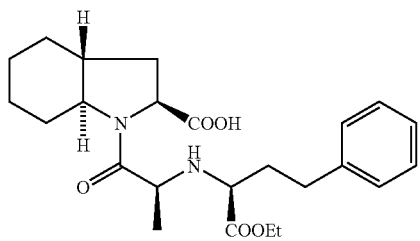

(2)

with a hydroxide compound in a saponification reaction solvent selected from water, C1-C4 alcohols and mixtures thereof at a temperature, and for a period of time, that is effective for permitting at least an almost complete saponification, wherein the hydroxide compound is an alkaline metal hydroxide, an alkaline-earth metal hydroxide, a tetraalkylammonium hydroxide or a substituted alkylammonium hydroxide, and wherein the Trandolapril, the hydroxide compound and the saponification reaction solvent are each employed in amounts that are effective for producing a reaction mixture that includes a salt of formula 3:

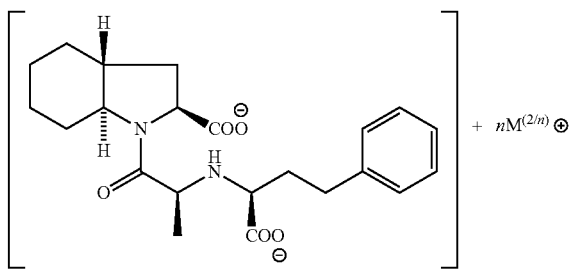

(3)

wherein M is an alkaline metal, an alkaline-earth metal, tetraalkylammonium or a substituted alkylammonium ion and n is 1 or 2;

(b) if the saponification reaction solvent employed in step (a) includes an alcohol other than n-butanol, removing such alcohol from the reaction mixture of step (a);

(c) if the reaction mixture of step (b) is not an aqueous solution, adding an amount of water to the reaction mixture that is effective for providing an aqueous solution;

(d) mixing the product of step (c) with an amount of acid, for a period of time, and at a temperature, that are effective for causing the pH of the mixture to reach its isoelectric point and providing Trandolaprilat in its free amino acid form;

(e) extracting Trandolaprilat in its free amino acid form from the mixture of step (d) with an amount of n-butanol, and at a temperature, that are effective for providing the Trandolaprilat in its free amino acid form in a solution containing n-butanol and water; and (f) removing an amount of water from the solution of step (e) that is sufficient to induce crystallization of the Trandolaprilat and provide crystalline Trandolaprilat in a polymorphic or pseudopolymorphic form.

The steps of the above process are described in more detail below.

Step (a)

Hydroxide Compound

The hydroxide compound that is employed in step (a) is preferably an alkaline metal hydroxide, an alkaline-earth metal hydroxide, a tetraalkylammonium hydroxide or a substituted alkylammonium hydroxide. Examples of these compounds are the same as those that are described hereinabove with respect to the procedure for preparing Trandolaprilat. The hydroxide compound is preferably an alkaline metal hydroxide, and is most preferably sodium hydroxide.

Saponification Reaction Solvent

The saponification reaction solvent that may be employed in step (a) includes the same saponification reaction solvents that are described hereinabove with respect to the procedure for preparing Trandolaprilat. The saponification reaction solvent employed in step (a) preferably is ethanol, water or a mixture of ethanol and water, and most preferably is a mixture of ethanol and water.

When the saponification reaction solvent is a mixture of a C1-C4 alcohol, such as ethanol, and water, the ratio between the C1-C4 alcohol and water may have a wide range, preferably from about 5:1 to about 1:5 by volume, and more preferably from about 2:1 to about 1:2 by volume, and still more preferably from about 1.2:1 to about 1:1.2 by volume, with a ratio of about 1/1 by volume being most preferred.

Amounts of Reactants and Solvent

The Trandolapril, hydroxide compound and saponification reaction solvent that are employed in step (a) are each employed in amounts that are effective for producing a reaction mixture that includes a salt of formula (3), as is described hereinabove. Such amounts can readily be determined by those of ordinary skill in the art. However, the amount of Trandolapril employed will preferably range from about 9 to about 14 percent.

In a preferred embodiment of this process, at least sufficient amounts of the hydroxide compound are employed that provide at least 2.0 equivalents of hydroxide in the reaction mixture. In another preferred embodiment, the hydroxide compound is provided in an amount that is in excess of the amount of Trandolapril employed, preferably in an amount of about 3.0 equivalents, more preferably in an amount of about 2.5 equivalents and most preferably in an amount of about 2.25 equivalents relative to the amount of Trandolapril employed.

Temperature

Step (a) is performed at a temperature that preferably is effective for permitting at least an almost complete saponification, and more preferably for permitting a complete saponification. The conversion may be monitored by methods known by those of ordinary skill in the art, such as HPLC. This temperature generally ranges from about 0° C. to about 40° C., and preferably ranges from about 15° C. to about 25° C., and more preferably ranges from about 20° C. to about 25° C. Higher temperatures may disadvantageously result in higher amounts of impurities being formed, which may be caused by an epimerization of the salt of formula (3) in the presence of excess hydroxide compound (base).

Time

Step (a) is performed for a period of time that preferably is effective for permitting at least an almost complete saponification, and more preferably for permitting a complete saponification. The time employed in step (a) typically ranges from about 5 to about 30 hours, and preferably ranges from about 10 to about 25 hours.

Salt of Formula 3

In the salt of formula (3) that is formed in step (a), M may be an alkaline metal, an alkaline-earth metal, a tetraalkylammonium ion or a substituted alkylammonium ion. Examples of these compounds are the same as those that are described hereinabove with respect to the procedure for preparing Trandolaprilat.

Steps (b) and (c)

If the selected saponification reaction solvent employed in step (a) is an alcohol, or a mixture of alcohol and water, and the alcohol employed alone or in the mixture is an alcohol other than n-butanol, the alcohol should be removed, which can be accomplished using methods known by those of ordinary skill in the art, such as by evaporation. Otherwise (if the only alcohol employed is n-butanol), it is not necessary to remove the alcohol. If the result of step (b) is not an aqueous solution, an amount of water that is effective for providing an aqueous solution should be added to the reaction mixture.

Step (d)

Acid

In step (d), the product of step (c) is mixed with an amount of acid that is effective for adjusting the pH of the mixture to reach its isoelectric point, and providing Trandolaprilat in its free amino acid form. Such a pH will generally range from about 3.6 to about 4.0. Such an amount of acid can readily be determined by those of ordinary skill in the art.

Acids that may be employed in step (d) for the acidification of the product of step (c) to the isoelectric point include, for example, those acids that are described hereinabove with respect to the procedure for preparing Trandolaprilat. Preferably, the acid employed is hydrochloric acid, and the hydrochloric acid is 2N aqueous hydrochloric acid.

Temperature

In step (d), the mixing of the acid with the product of step (c) preferably occurs at a temperature that is effective for causing the pH of the mixture to reach its isoelectric point, and providing Trandolaprilat in its free amino acid form. Such temperature generally ranges from about 20° C. to about 80° C., and preferably ranges from about 30° C. to about 70° C., and more preferably ranges from about 60° C. to about 70° C.

Time

In step (d), the mixing of the acid with the product of step (c) preferably occurs for a period of time that is effective for causing the pH of the mixture to reach its isoelectric point, and providing Trandolaprilat in its free amino acid form.

Step (e)

In step (e), Trandolaprilat in its free amino acid form is extracted from the mixture of step (d) with an amount of n-butanol, or an azeotropic mixture of n-butanol and water, and at a temperature, that are effective for providing the Trandolaprilat in its free amino acid form in a solution or bi-phasic mixture containing n-butanol and water.

The extraction may be performed at a temperature ranging from about room temperature to about the boiling point of an azeotropic n-butanol/water mixture, preferably between about room temperature and about 70° C., and more preferably from about 50° C. to about 60° C.

The amount of n-butanol or the azeotropic mixture of n-butanol and water that should be employed generally ranges from about 5:1 to about 1:5, and preferably ranges from about 2:1 to about 1:2, and most preferably is about 1:1.

Step (f)

In step (f), an amount of water is removed from the solution of step (e) that is sufficient for inducing crystallization of the Trandolaprilat and provide crystalline Trandolaprilat in a polymorphic or pseudopolymorphic form. Because Trandolaprilat is not soluble in anhydrous n-butanol, its crystallization from the organic layer can be initiated by removing the water, for example, by concentrating an n-butanol/water solution containing the Trandolaprilat using azeotropic distillation (to provide crystalline Trandolaprilat).

If necessary to obtain a desired Trandolaprilat product, the product of step (f) may, optionally, be dried at a temperature and pressure, and for a period of time, that are effective for providing crystalline Trandolaprilat in a pseudopolymorphic form.

Purity and Yield

The Trandolaprilat produced by this process is generally obtained as a substantially pure crystalline form in a yield of at least about 92%. Such Trandolaprilat has been obtained having a purity greater than 99.5%. Purity was determined by HPLC using a Luna C18 (150×4.6 mm, 3 µm; Manufacturer: Phenomenex, Torrence, Calif., USA) column, as well as a Symmetry C18(2) (150×4.6 mm, 3.5 µm; Manufacturer: Waters Corporation, Millford, Mass., USA) column using as mobile phase: Mobile phase A: 0.03% v/v of trifluoroacetic acid in water; Mobile phase B: 0.025% v/v of trifluoroacetic acid in acetonitrile; column temperature 30° C., flow rate: 1.5 ml/min, detection: UV 206 nm; eluent gradient:

| Time [min] | % of A | % of B |
|---|---|---|
| 0 | 90 | 10 |
| 20.00 | 10.0 | 90.0 |
| 25.00 | 10.0 | 90.0 |

Purity was determined in the same manner, and using the same equipment, in the various other experiments that are discussed throughout this document.

Procedure for The Preparation and Isolation of Crystalline Trandolaprilat in a Polymorphic or Pseudopolymorphic Form—(Second Procedure)

In another aspect, the present invention provides a novel process for the preparation and isolation of crystalline Trandolaprilat in a polymorphic or pseudopolymorphic form, including crystalline Trandolaprilat Form B (a pseudopolymorph of Trandolaprilat), crystalline Trandolaprilat Form C (a pseudopolymorph of Trandolaprilat) and crystalline Trandolaprilat Form D (a pseudopolymorph of Trandolaprilat), or as a mixture of at least two different forms of crystalline Trandolaprilat. This process commences with the saponification of Trandolapril in a suitable solvent using a hydroxide compound. The crystalline Trandolaprilat compound, or mixture of crystalline Trandolaprilat compounds, is then isolated by crystallization from the reaction mixture after adjusting the pH of the mixture to the isoelectric point.

This aspect of the invention is a process for producing Trandolaprilat in a substantially pure crystalline form (as a polymorph or pseudopolymorph), or as a mixture of at least two different crystalline forms, comprising the steps of:

(a) reacting Trandolapril (2):

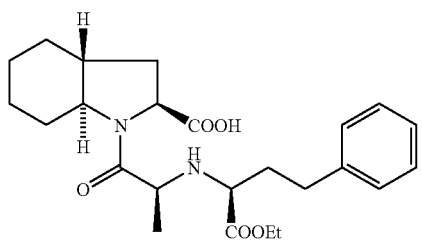

(2)

with a hydroxide compound in a saponification reaction solvent selected from water, C1-C4 alcohols and mixtures thereof at a temperature, and for a period of time, that is effective for permitting at least an almost complete saponification, wherein the hydroxide compound is an alkaline metal hydroxide, an alkaline-earth metal hydroxide, a tetraalkylammonium hydroxide or a substituted alkylammonium hydroxide, wherein the Trandolapril, the hydroxide compound and the saponification reaction solvent are each employed in amounts that are effective for producing a reaction mixture that includes a salt of formula 3:

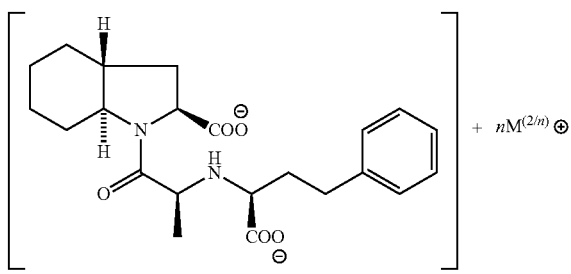

(3)

wherein M is an alkaline metal, an alkaline-earth metal, tetraalkylammonium or a substituted alkylammonium ion and n is 1 or 2;

(b) if the saponification reaction solvent employed in step (a) includes a C4 alcohol, removing the C4 alcohol from the reaction mixture of step (a);

(c) if the reaction mixture of step (b) is not an aqueous solution, adding an amount of water to the reaction mixture that is effective for providing an aqueous solution;

(d) mixing the product of step (c) with an amount of an acid, and for a period of time, and at a temperature, that are effective for causing the pH of the mixture to reach its isoelectric point and providing Trandolaprilat in a substantially pure free amino acid form;

(e) separating the product of step (d) from the supernatant; and (f) drying the product of step (e) to provide Trandolaprilat in a substantially pure crystalline form, or as a mixture of at least two different crystalline forms.

The steps of the above process are described in more detail below.

Step (a)

Hydroxide Compound

The hydroxide compound that is employed in step (a) is preferably an alkaline metal hydroxide, an alkaline-earth metal hydroxide, a tetraalkylammonium hydroxide or a substituted alkylammonium hydroxide. Examples of these compounds are the same as those that are described hereinabove with respect to the procedure for preparing Trandolaprilat. The hydroxide compound is preferably an alkaline metal hydroxide, and is most preferably sodium hydroxide.

Saponification Reaction Solvent

The saponification reaction solvent that may be employed in step (a) includes the same saponification reaction solvents that are described hereinabove with respect to the procedure for preparing Trandolaprilat. The saponification reaction solvent employed in step (a) preferably is ethanol, water or a mixture of ethanol and water, and most preferably is a mixture of ethanol and water.

In step (a), if the saponification reaction solvent comprises a mixture of a C1-C4 alcohol, such as methanol, and water, the ratio between the C1-C4 alcohol and water may have a wide range, preferably from about 5:1 to about 1:5 by volume, and more preferably from about 2:1 to about 1:2 by volume, and still more preferably from about 1/1 to about 1/1.5 by volume, with a ratio of about 1/1 by volume being most preferred.

Amounts of Reactants and Solvent

The Trandolapril, hydroxide compound and saponification reaction solvent that are employed in step (a) are each employed in amounts that are effective for producing a reaction mixture that includes a salt of formula (3), as is described hereinabove. Such amounts can readily be determined by those of ordinary skill in the art. However, as described above, preferably the Trandolapril starting material is utilized in the reaction mixture at a concentration in the range of from about 9 to about 14 percent. The amount of hydroxide compound is also as described above.

In a preferred embodiment of this process, at least sufficient amounts of the hydroxide compound are employed that provide at least 2.0 equivalents of hydroxide in the reaction mixture (calculated on the amount of Trandolapril that is employed). In another preferred embodiment, the hydroxide compound is provided in an amount that is in excess of the amount of Trandolapril employed, preferably in an amount of about 3.0 equivalents, more preferably in an amount of about 2.5 equivalents and most preferably in an amount of about 2.2 equivalents relative to the amount of Trandolapril employed.

Temperature

Step (a) is performed at a temperature that preferably is effective for permitting at least an almost complete saponification, and more preferably for permitting a complete saponification. The conversion may be monitored by methods known by those of ordinary skill in the art, such as HPLC. This temperature generally ranges from about 0° C. to about 40° C., and preferably ranges from about 15° C. to about 25° C., and more preferably ranges from about 20° C. to about 25° C. Higher temperatures may disadvantageously result in higher amounts of impurities being formed, which may be caused by an epimerization of the salt of formula (3) in the presence of excess hydroxide compound (base).

Salt of Formula 3

In the salt of formula (3) that is formed in step (a), M may be an alkaline metal, an alkaline-earth metal, a tetraalkylammonium ion or a substituted tetraalkylammonium ion. Examples of these compounds are the same as those that are described hereinabove with respect to the procedure for preparing Trandolaprilat.

Step (b)

If the saponification reaction solvent employed in step (a) includes a C4 alcohol, the C4 alcohol is preferably removed from the reaction mixture of step (a) in step (b) is removed preferably by distillation.

Step (c)

If the reaction mixture of step (b) is not an aqueous solution, an amount of water is preferably added to the reaction mixture of step (b) that is effective for providing an aqueous solution of Trandolaprilat.

Step (d)

Acid

The product of step (c) is mixed with an amount of an acid, and for a period of time, and at a temperature, that are effective for causing the pH of the mixture to reach its isoelectric point (e.g., pH 3.6 to 4.0) and providing Trandolaprilat in a substantially pure free amino acid form, or as a mixture of at least two different free amino acid forms.

Acids that may be employed in step (d) for the acidification of the product of step (c) to the isoelectric point include, for example, those acids that are described hereinabove with respect to the procedure for preparing Trandolaprilat. Preferably, the acid employed is hydrochloric acid, and the hydrochloric acid is 2N aqueous hydrochloric acid.

Temperature

In step (d), the mixing of the acid with the product of step (c) preferably occurs at a temperature that is effective for causing the pH of the mixture to reach its isoelectric point, and providing Trandolaprilat in its free amino acid form, or as a mixture of at least two different free amino acid forms. Such temperature generally ranges from about 0° C. to about 40° C., and preferably ranges from about 15° C. to about 25° C., and more preferably is approximately room temperature.

Time

In step (d), the mixing of the acid with the product of step (c) preferably occurs for a period of time that is effective for causing the pH of the mixture to reach its isoelectric point, and providing Trandolaprilat in its free amino acid form, or as a mixture of at least two different free amino acid forms.

Step (e)

The product of step (c) is separated from the supernatant, which may by filtration, centrifugation or similar process.

Step (f)

The product of step (e) is dried to provide Trandolaprilat in a substantially pure crystalline form, or as a mixture of at least two different crystalline forms.

Temperature

Step (e) is performed at a temperature that preferably is effective for providing Trandolaprilat in a substantially pure crystalline form, or as a mixture of at least two different crystalline forms. This temperature generally ranges from about 0° C. to about 40° C., and preferably ranges from about 10° C. to about 30° C., and more preferably ranges from about 20° C. to about 25° C. Conveniently at room temperature.

Purity and Yield

The Trandolaprilat produced by this process is generally obtained as a substantially pure crystalline form, or as a mixture of at least two different crystalline forms, in yields of about $\geq 90\%$. It can be obtained as a substantially pure crystalline form having a purity, as determined by HPLC, of about $\geq 99\%$ In a most preferred way to prepare Trandolaprilat from Trandolapril according to this method, from about a 9% to about a 14% solution of a salt of formula (3), wherein M=Na, in a mixture of ethanol/water having a volume ratio of about 1/1 is acidified with 2N aqueous hydrochloric acid to a pH ranging from about 3.6 to about 4.0. During acidification, the crystallization of Trandolaprilat starts at a pH between about 4.5 and about 5.0 after seeding.

In the method described in the preceding paragraph, the volume ratio of the mixture of ethanol and water is important. For example, if a 9% solution of a salt of formula (3), wherein M=Na, in a mixture of ethanol/water having a volume ratio of $1/\geq 2$ is acidified with 2N aqueous hydrochloric acid to a pH ranging from about 3.6 to about 4.0 at a temperature ranging from about 20° C. to about 25° C., then initially a resin or a gum precipitates, which slowly crystallizes during stirring at this temperature. A formation of a resin or a gum can cause problems when producing Trandolaprilat on a technical scale during stirring. If, in contrast, the volume ratio of ethanol/water is $\geq 1/1$, a simultaneous precipitation of inorganic salts (formed during the acidification) may contaminate the final product.

In this method, the concentration of the solution containing a salt of formula (3) is also important. If the crystallization is performed with an acidification from a more concentrated solution (>14%) of a salt of formula (3), wherein M=Na, in a 1/1 mixture of ethanol/water, a thick and difficultly stirrable suspension may be formed. If, in contrast, the crystallization is performed with an acidification from a less concentrated solution (<9%) of a salt of formula (3), wherein M=Na, in a 1/1 mixture of ethanol/water, there may be some loss of yield of the final product (more than would otherwise occur).

Another preferred method for producing Trandolaprilat in a substantially pure crystalline form, or as a mixture of crystalline forms, including crystalline Trandolaprilat Form B, crystalline Trandolaprilat Form C, crystalline Trandolaprilat Form D, and mixtures thereof, comprises:

(a) reacting Trandolapril with at least 2.0 equivalents of NaOH in a saponification reaction solvent including ethanol and water in a ratio of from about 1/1 to about 1/1.5 by volume at a temperature ranging from about 20° C. to about 25° C. for a period of time that is sufficient for producing a reaction mixture that includes a salt of formula 3:

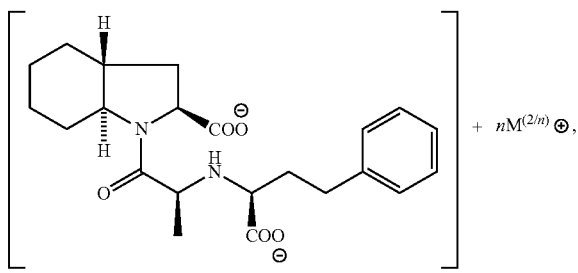

(3)

wherein M is sodium and n is 2;

(b) adjusting the pH of the product of step (a) with hydrochloric acid to a range from about 3.6 to about 4.0 to provide Trandolaprilat in a substantially pure free amino acid form, or as a mixture of at least two different free amino acid forms;

(c) separating the product of step (b) from the supernatant; and (d) drying the product of step (c) to provide Trandolaprilat in a substantially pure crystalline form, or as a mixture of at least two different crystalline forms.

Steps (a)-(d) of the above process may be performed in the same manner described hereinabove in connection with the Second Procedure.

Procedure for The Preparation and Isolation of Crystalline Trandolaprilat Form E Crystalline Trandolaprilat Form E (a polymorph of Trandolaprilat) may be prepared from crystalline Trandolaprilat Form B (a pseudopolymorph of Trandolaprilat) by a process comprising drying crystalline Trandolaprilat Form B at a temperature and pressure, and for a period of time, that are effective for removing ethanol that is bound to crystals present in the crystalline Trandolaprilat Form B.

Prior to the drying of the crystalline Trandolaprilat Form B, the crystalline Trandolaprilat Form B may be advantageous to reduce the particle size by, e.g. milling or grinding.

Crystalline Forms of Trandolaprilat

In another aspect, the present invention provides novel crystalline forms of Trandolaprilat.

The present invention provides Trandolaprilat in a crystalline form comprising a structure of formula (4):

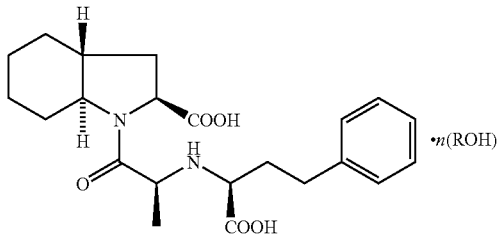

(4)

wherein R is H or a C1-C4 alkyl and n ranges from 0 to 2, and may be stoichiometric or non-stoichiometric.

In one preferred embodiment, in formula (4), R is H and n is 1 or non-stoichiometric. This crystalline form of Trandolaprilat is referred to as a "hydrate" (a pseudopolymorph).

In a second preferred embodiment, in formula (4), R is H and n is greater than 1 and is non-stoichiometric.

In a third preferred embodiment, in formula (4), R is a C1-C4 alkyl (preferably ethyl or butyl) and n is 2. This crystalline form of Trandolaprilat is referred to as a "solvate" (a pseudopolymorph).

In a fourth preferred embodiment, in formula (4), n is 0. This crystalline form of Trandolaprilat is referred to as a "non-solvate" (a polymorph).

The novel crystalline forms of Trandolaprilat of the invention include crystalline Trandolaprilat Form A, crystalline Trandolaprilat Form B, crystalline Trandolaprilat Form C, crystalline Trandolaprilat Form D and crystalline Trandolaprilat Form E, which are discussed hereinabove.

Via experimentation, it has surprisingly and unexpectedly been discovered that Trandolaprilat may be produced not only in polymorphic forms, but also in a variety of different pseudopolymorphic forms, particularly if it is crystallized from hydroxylic solvents, such as water and/or alcohols. Trandolaprilat appears to have a high tendency to be produced in various crystalline pseudopolymorphic forms, particularly if it is crystallized from hydroxylic solvents.

Crystalline Trandolaprilat, for example, that is produced according to the "First Procedure" described hereinabove can be obtained in a crystalline (pseudopolymorphic) form containing two molecules of n-butanol in the crystal unit (crystalline Trandolaprilat Form A), which preferably is substantially pure.

Crystalline Trandolaprilat that is crystallized according to the "Second Procedure" described hereinabove from hydroxylic solvents such as water, alcohols or mixtures of water and alcohol(s) can be obtained in different crystalline forms, such as crystalline Trandolaprilat Form B, crystalline Trandolaprilat Form C and crystalline Trandolaprilat Form D, which are also preferably substantially pure, or as mixtures of two or more crystalline forms. Crystalline Trandolaprilat Form E can be produced from crystalline Trandolaprilat Form B in the manner described hereinabove.

Substantially pure forms of crystalline Trandolaprilat (as well as less pure forms) can generally be obtained by crystallizing from pure hydroxylic solvents.

Mixtures of two or more different forms of crystalline Trandolaprilat can generally be obtained by crystallizing from a mixture of two or more hydroxylic solvents, such as a mixture of water and ethanol. The production of such mixtures is more complicated because of the high tendency of Trandolaprilat to crystallize as pseudopolymorphic forms with different hydroxylic solvents. This can be explained by the fact that pseudopolymorphic forms of crystalline Trandolaprilat have at least one more variance than polymorphic forms and, therefore, further parameters, such as the composition of the solvent system, must also be considered. For this reason, the second process may deliver Trandolaprilat not only in substantially pure crystalline forms, but also as a mixture of at least two different crystalline Trandolaprilat forms if solvent mixtures are used for the crystallization. The favored Trandolaprilat crystalline form is controlled by thermodynamic stabilities of the respective Trandolaprilat crystalline form, as well as by kinetic effects during the crystallization. In other words, if a solvent mixture is used for the crystallization, the purity and composition of the two or more crystalline Trandolaprilat forms in the final product depends upon the ratio of the solvents employed, as well as upon the variation of the rate of crystallization. Slower crystallizations may provide thermodynamically stable crystalline Trandolaprilat forms, whereas a fast precipitation may provide kinetically favored crystalline Trandolaprilat forms. Stirring time, temperature during the crystallization or slurry of Trandolaprilat and the drying conditions may have further influences on the purity and composition of various crystalline forms of crystalline Trandolaprilat. If Trandolaprilat, for example, is crystallized according to the "Second Procedure" from mixtures of ethanol and water in different ratios, then the isolated crystalline Trandolaprilat may contain variable amounts of water, which typically range from about 0.63% to about 4.2% (with the latter corresponding to the monohydrate form), as well as variable amounts of ethanol, which typically range from about 0.2% to about 19% (with the latter corresponding to the disolvate form with ethanol), which indicates the formation of different crystalline forms of Trandolaprilat or mixtures thereof. Parameters as described hereinabove, such as ratio of ethanol/water employed for the crystallization step, variation of rate of crystallization, stirring temperature and stirring time of the suspension after crystallization and the drying conditions (temperature, pressure, time and the like) have important influences on the composition of crystalline forms in Trandolaprilat. Using information that is provided herein, and information that is known, those of ordinary skill in the art can readily vary one or more of these conditions to produce a desired form of crystalline Trandolaprilat, or a mixture of two or more of these crystalline forms.

The solid forms of the crystalline Trandolaprilat of the present invention may exist as substantially pure crystalline Trandolaprilat forms or as mixtures of two or more crystalline Trandolaprilat forms, each of which shows, and can be identified by, its own (unique) X-ray diffraction profile characteristics upon X-ray diffraction.

Crystalline Trandolaprilat Form A

Crystalline Trandolaprilat Form A is a pseudopolymorphic form of Trandolaprilat that contains 2 equivalents of n-butanol bound in its crystalline structure (i.e., it is a disolvate with n-butanol).

Figure 2:
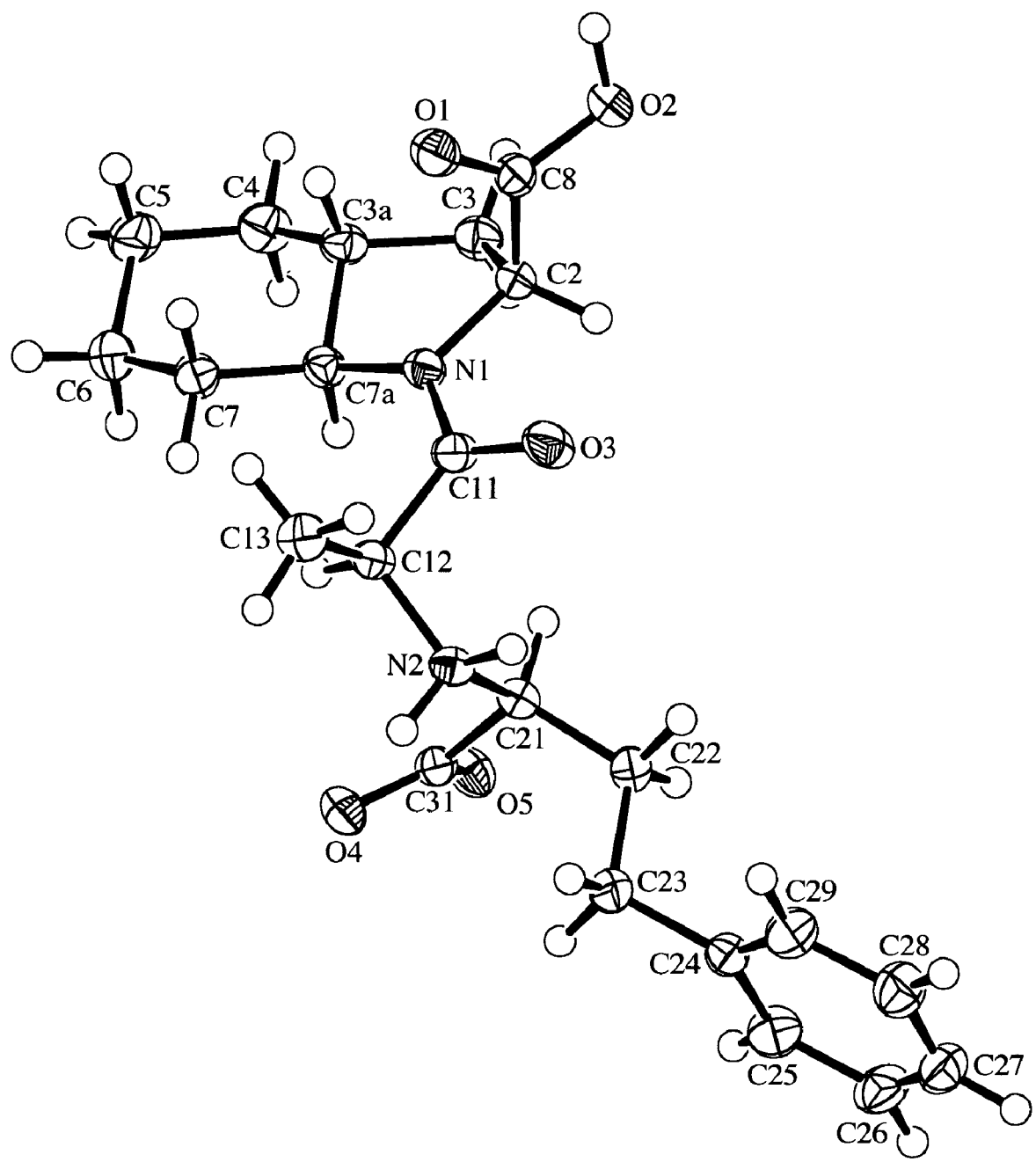
FIG. 2 is a drawing of the crystal structure obtained from X-ray measurements of Trandolaprilat Form A.

Crystalline Trandolaprilat Form A has the X-ray powder diffraction data shown in Table 1, the crystallographic data and structure parameter shown in Table 2, the X-Ray powder diffraction pattern shown in FIG. 1 and the crystal structure (obtained from X-ray measurements of the compound) shown in FIG. 2. The intensities of the various X-ray powder diffraction peaks that are described and/or shown throughout this document may vary due to texture or other effects, as is known by those of skill in the art. Further, those having skill in the art will recognize that the 2theta positions in the powder patterns for a specific crystalline form of the same substance may vary within a margin of error generally derived, for example, from the measuring accuracy of the particular X-ray diffractometer employed. Finally, an entire peak profile can vary by partially greater degree due to sample preparation, variations in density of packed samples and the like. While the x-ray powder diffraction data that are set forth in the tables that are present in this document are based upon actual experimental results, the numbers in several of the columns have been rounded in a conventional manner to one place after the decimal point, and a variation of up to about +/−0.20 would reasonably be expected. For example, a variation of about +/−0.20 degrees 2-theta at any one or more of the peaks would be reasonably expected. All X-ray powder diffraction analyses that are described and/or shown herein were performed using a Philips PW1800 diffractometer equipped with a Xe-proportional detector (generator settings=30 mA, 40 kV), as well as Bruker AXS D8 Advance (generator settings=40 mA, 40 kV) equipped with a VÅNTEC-1 detector: radiation: CuKα; angle range 2theta=2°/3° to 40°; step size=0.02°; the scan step time ranged for the various measurements from 1 s to 4 s.

Figure 3:
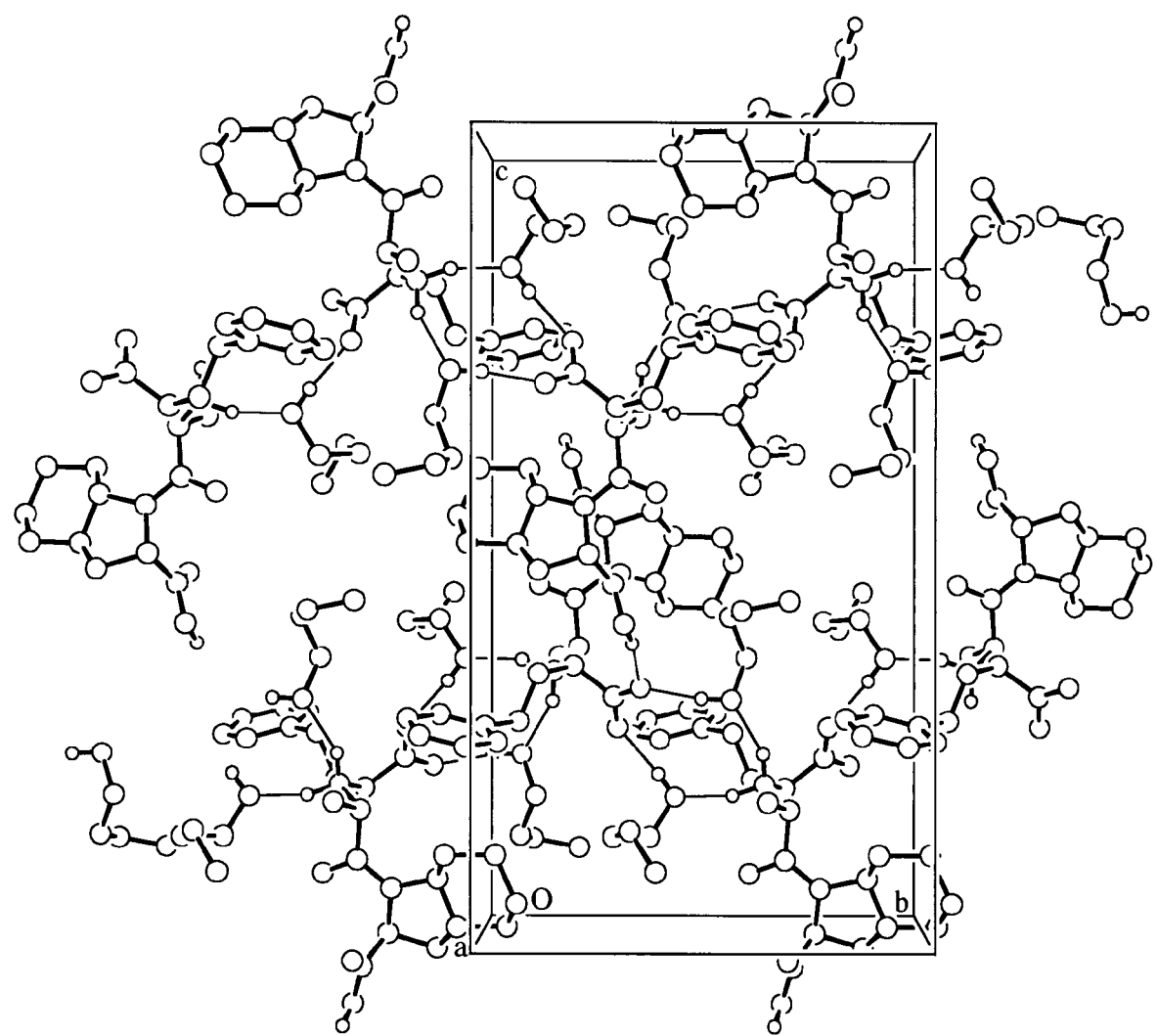
FIG. 3 is a drawing of an asymmetric unit of Trandolaprilat Form A, which contains one molecule of Trandolaprilat and two molecules of n-butanol bound to the crystalline structure.
Figure 4:
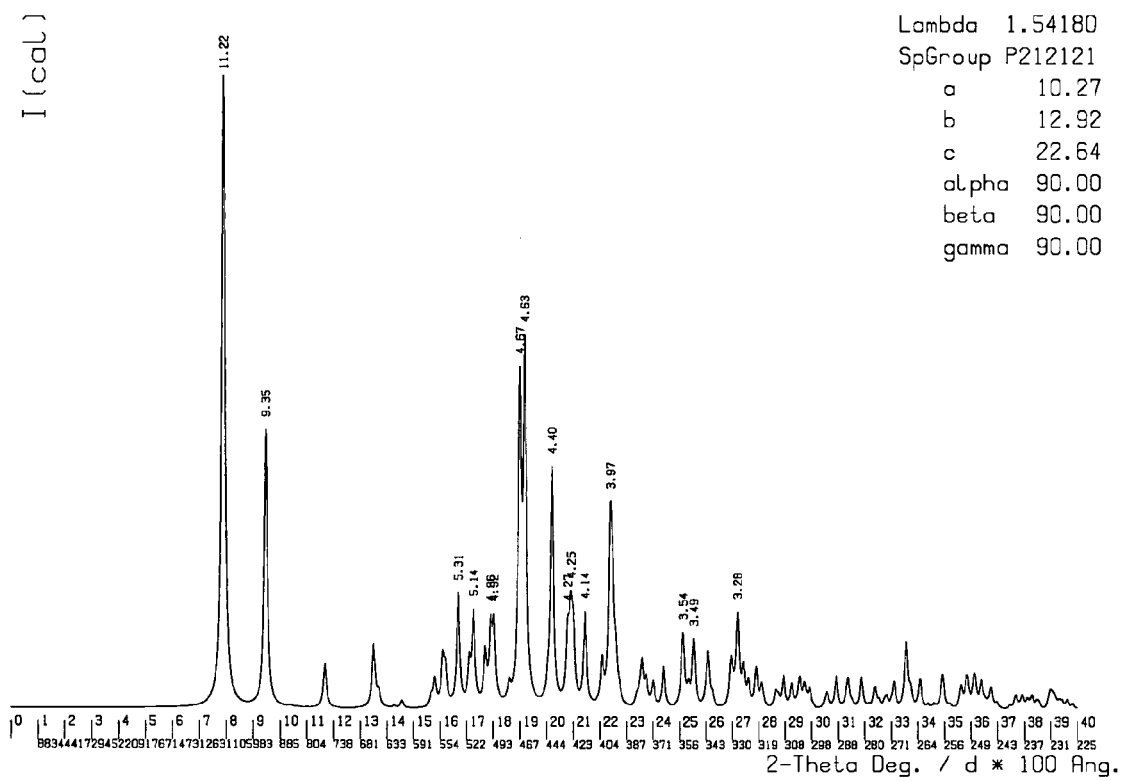
FIG. 4 is a graph that shows the calculated powder profile from crystal data of Trandolaprilat Form A.

FIG. 3 shows an asymmetric unit of Crystalline Trandolaprilat Form A (containing one molecule of Trandolaprilat and two molecules of n-butanol), and FIG. 4 shows the calculated powder profile from crystal data of Crystalline Trandolaprilat Form A (Trandolaprilat disolvate with 2 n-butanol).

Crystalline Trandolaprilat Form A can be produced using the "First Procedure" described hereinabove, and according to Example 1, by azeotropic distillation of a solution of Trandolaprilat in n-butanol saturated with water (i.e., using a mixture of the solvents n-butanol and water), which initiates its crystallization. Because Trandolaprilat is generally not soluble in anhydrous n-butanol, removal of the water from the solvent mixture, for example, by azeotropic distillation initiate its crystallization. The desired product can be obtained in a substantially pure crystalline form containing 2 equivalents of n-butanol in the crystal structure.

TABLE 1

Powder X-Ray Diffraction Data of Crystalline Trandolaprilat Form A

| Pos. [°2Th.] | Height [cts] | d-spacing [Å] | Rel. Int. [%] |
|---|---|---|---|
| 7.7 | 15534 | 11.5 | 100.0 |
| 9.2 | 2211 | 9.6 | 14.2 |
| 11.4 | 325 | 7.7 | 2.1 |
| 13.2 | 913 | 6.7 | 5.9 |
| 13.5 | 421 | 6.6 | 2.7 |
| 14.3 | 84 | 6.2 | 0.5 |
| 15.6 | 1898 | 5.7 | 12.2 |
| 15.9 | 1087 | 5.6 | 7.0 |
| 16.4 | 1891 | 5.4 | 12.2 |
| 16.9 | 1068 | 5.3 | 6.9 |
| 17.3 | 1246 | 5.1 | 8.0 |
| 17.7 | 1481 | 5.0 | 9.5 |
| 18.2 | 503 | 4.9 | 3.2 |
| 18.6 | 4220 | 4.8 | 27.2 |
| 18.9 | 4715 | 4.7 | 30.4 |
| 19.8 | 3656 | 4.5 | 23.5 |
| 20.6 | 4538 | 4.3 | 29.2 |
| 21.2 | 1141 | 4.2 | 7.3 |
| 22.0 | 5420 | 4.0 | 34.9 |
| 22.2 | 2072 | 4.0 | 13.3 |
| 23.3 | 1242 | 3.8 | 8.0 |
| 23.7 | 731 | 3.8 | 4.7 |
| 23.9 | 491 | 3.7 | 3.2 |
| 24.6 | 1117 | 3.6 | 7.2 |
| 25.2 | 997 | 3.5 | 6.4 |
| 25.7 | 1055 | 3.5 | 6.8 |
| 26.7 | 1383 | 3.3 | 8.9 |
| 27.0 | 1773 | 3.3 | 11.4 |
| 27.5 | 663 | 3.2 | 4.3 |
| 28.6 | 645 | 3.1 | 4.2 |
| 29.0 | 667 | 3.1 | 4.3 |
| 29.5 | 264 | 3.0 | 1.7 |
| 30.0 | 152 | 3.0 | 0.9 |
| 30.5 | 828 | 2.9 | 5.3 |
| 30.9 | 576 | 2.9 | 3.7 |
| 31.6 | 707 | 2.8 | 4.6 |
| 32.0 | 796 | 2.8 | 5.1 |
| 32.7 | 893 | 2.8 | 5.8 |
| 33.0 | 597 | 2.7 | 3.8 |
| 33.7 | 1154 | 2.6 | 7.4 |
| 34.1 | 250 | 2.6 | 1.6 |
| 34.4 | 251 | 2.6 | 1.6 |
| 35.1 | 748 | 2.6 | 4.8 |
| 35.9 | 881 | 2.5 | 5.7 |
| 36.2 | 576 | 2.5 | 3.7 |
| 38.3 | 355 | 2.4 | 2.3 |
| 38.7 | 316 | 2.3 | 2.0 |
| 39.4 | 140 | 2.3 | 0.9 |

TABLE 2

Crystallographic Data and Structure Parameter of Crystalline Trandolaprilat Form A

| | |
|---|---|
| Crystallized from | H$_2$O/n-BuOH |
| Empirical formula | C$_{30}$H$_{50}$N$_2$O$_7$ |
| Formula weight [g mol$^{-1}$] | 550.73 |
| Crystal colour, habit | colorless, prism |
| Crystal dimensions [mm] | 0.20 × 0.28 × 0.32 |
| Temperature [K] | 160(1) |
| Crystal system | orthorhombic |
| Space group | P2$_1$2$_1$2$_1$ (#19) |
| Z | 4 |
| Reflections for cell determination | 3887 |
| 2θ range for cell determination [°] | 4-55 |
| Unit cell parameters    a [Å] | 10.2709(2) |
|              b [Å] | 12.9233(2) |
|              c [Å] | 22.6409(3) |
|              α [°] | 90 |
|              β [°] | 90 |
|              γ [°] | 90 |
|              V [Å$^3$] | 3005.22(8) |
| F(000) | 1200 |
| D$_x$ [g cm$^{-3}$] | 1.217 |
| μ(Mo Kα) [mm$^{-1}$] | 0.0855 |
| Scan type | ø and ω |
| 2θ$_{(max)}$ [°] | 55 |
| Total reflections measured | 45353 |
| Symmetry independent reflections | 3864 |
| R$_{int}$ | 0.051 |
| Reflections with I > 2σ(I) | 3418 |
| Reflections used in refinement | 3858 |
| Parameters refined | 376 |
| Final R(F) [I > 2σ(I) reflections] | 0.0417 |
| wR(F$^2$) (all data) | 0.1100 |
| Weights: | w = [σ$^2$(F$_o^2$) + (0.0562P)$^2$ + 0.8633P]$^{-1}$ where P = (F$_o^2$ + 2F$_c^2$)/3 |
| Goodness of fit | 1.039 |
| Secondary extinction coefficient | 0.012(1) |
| Final Δ$_{max}$/σ | 0.001 |
| Δρ (max; min) [e Å$^{-3}$] | 0.46; −0.23 |
| σ(d$_{C-C}$) [Å] | 0.003-0.005 |

Crystalline Trandolaprilat Form B

Figure 5:
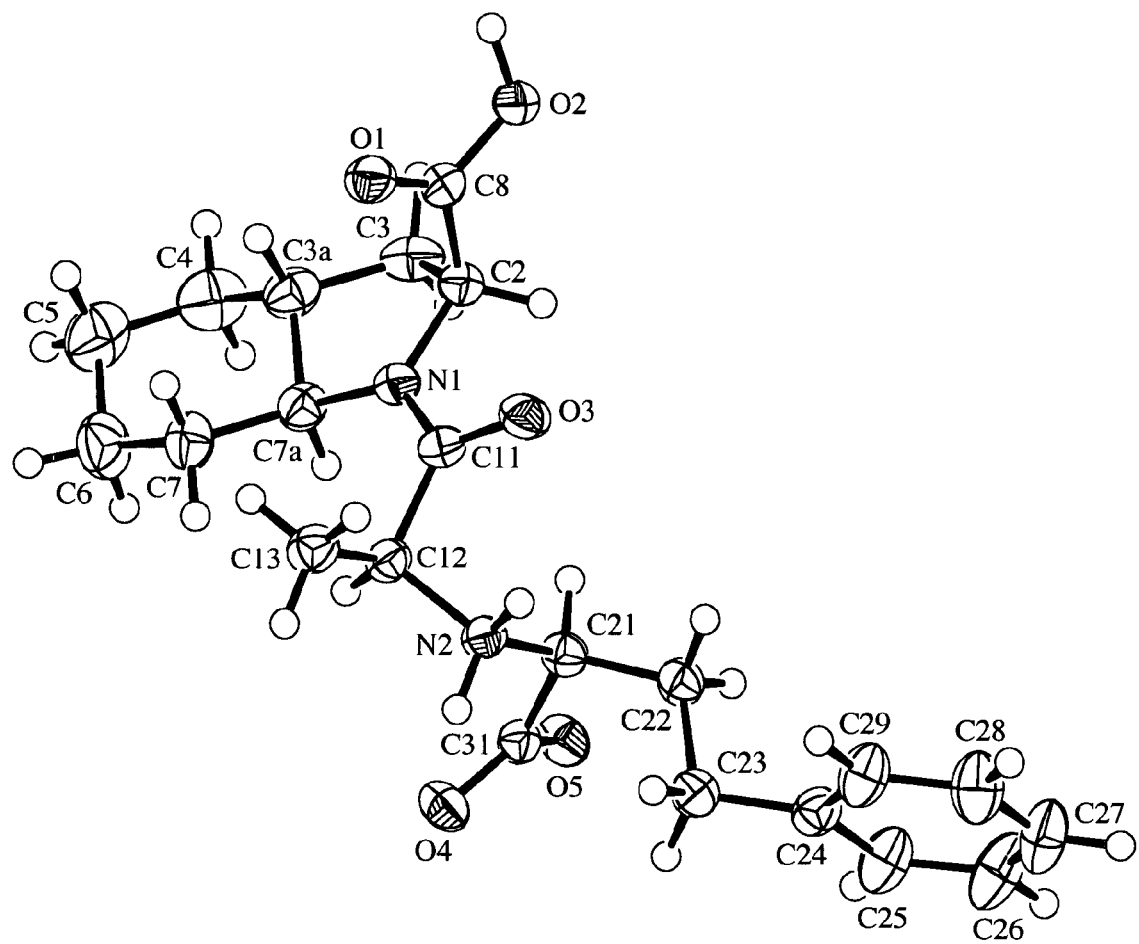
FIG. 5 is a drawing of the crystal structure obtained from X-ray measurements of Trandolaprilat Form B.
Figure 6:
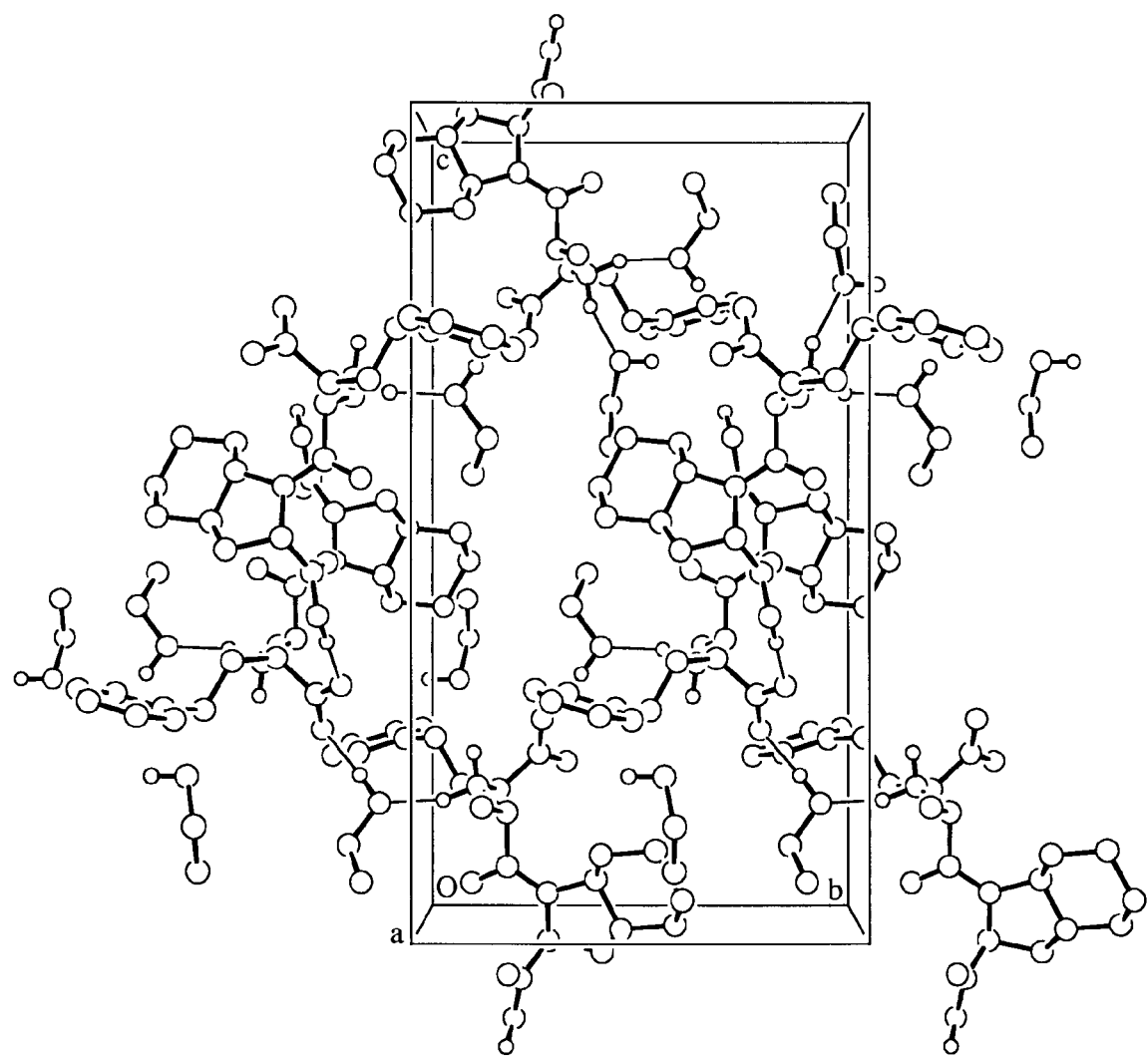
FIG. 6 is a drawing of an asymmetric unit of Trandolaprilat Form B, which contains one molecule of Trandolaprilat and two molecules of ethanol bound to the crystalline structure.
Figure 7:
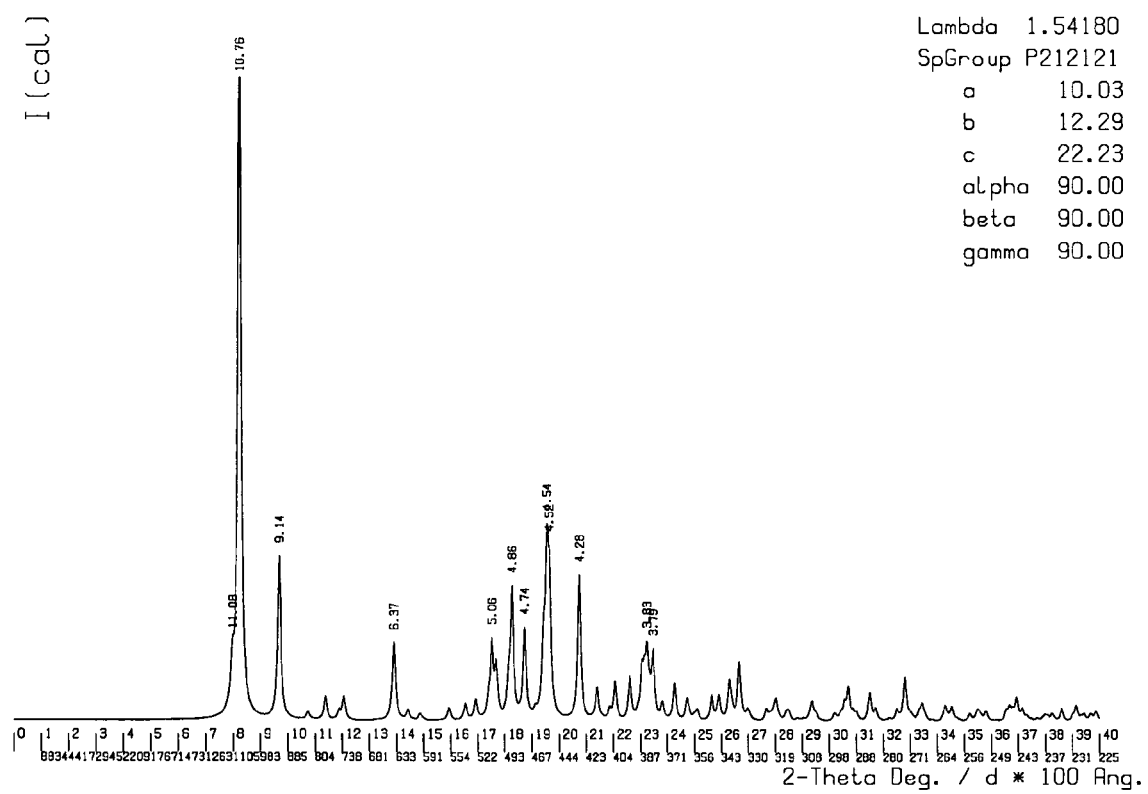
FIG. 7 is a graph that shows the calculated powder profile from crystal data of Trandolaprilat Form B.

Crystalline Trandolaprilat Form B is a pseudopolymorphic form of Trandolaprilat that contains 2 equivalents of ethanol bound in its crystalline structure (i.e., it is a disolvate with ethanol). It has the X-ray powder diffraction data shown in Table 10, the X-ray powder diffraction pattern shown in FIG. 13, the X-ray diffraction data crystal structure shown in FIGS. 5 and 6, the crystallographic data and structure parameters shown in Table 3, and the calculated powder profile shown in FIG. 7.

Crystalline Trandolaprilat Form B can be produced using the "Second Procedure" described hereinabove, and according to Examples 2 and 5, with a crystallization/slurry of Trandolapril in ethanol, as well as by slow crystallization of Trandolapril from diluted ethanol/water mixtures. The desired product can be obtained in a substantially pure crystalline form containing 2 equivalents of ethanol in the crystal structure.

TABLE 10

Powder X-Ray Diffraction Data of Crystalline Trandolaprilat Form B

| Pos. [°2Th.] | Height [cts] | d-spacing [Å] | Rel- Int. [%] |
|---|---|---|---|
| 8.1 | 485321 | 10.9 | 100 |
| 9.6 | 251491 | 9.2 | 51.8 |
| 10.6 | 22079 | 8.3 | 4.5 |
| 11.3 | 49787 | 7.9 | 10.3 |

TABLE 10-continued

Powder X-Ray Diffraction Data of Crystalline Trandolaprilat Form B

| Pos. [°2Th.] | Height [cts] | d-spacing [Å] | Rel- Int. [%] |
|---|---|---|---|
| 11.9 | 38231 | 7.4 | 7.9 |
| 13.8 | 110823 | 6.4 | 22.8 |
| 14.8 | 41587 | 6.0 | 8.6 |
| 15.9 | 39706 | 5.6 | 8.2 |
| 16.6 | 50332 | 5.3 | 10.4 |
| 17.4 | 178820 | 5.1 | 36.8 |
| 18.1 | 211405 | 4.9 | 43.6 |
| 18.4 | 140642 | 4.8 | 29.0 |
| 19.3 | 430165 | 4.6 | 88.6 |
| 20.5 | 241048 | 4.3 | 49.7 |
| 21.2 | 108775 | 4.2 | 22.4 |
| 21.6 | 99472 | 4.1 | 20.5 |
| 22.4 | 103529 | 4.0 | 21.3 |
| 22.9 | 256485 | 3.9 | 52.8 |
| 23.9 | 94042 | 3.7 | 19.4 |
| 24.4 | 70724 | 3.6 | 14.6 |
| 24.8 | 60099 | 3.6 | 12.4 |
| 25.5 | 99950 | 3.5 | 20.6 |
| 26.0 | 95754 | 3.4 | 19.7 |
| 26.5 | 111361 | 3.4 | 22.9 |
| 27.5 | 75690 | 3.3 | 15.6 |
| 27.7 | 81574 | 3.2 | 16.8 |
| 28.6 | 68696 | 3.1 | 14.2 |
| 29.4 | 53969 | 3.0 | 11.1 |
| 30.0 | 91367 | 3.0 | 18.8 |
| 30.6 | 70719 | 2.9 | 14.6 |
| 32.1 | 92500 | 2.8 | 19.1 |
| 33.9 | 90615 | 2.6 | 18.7 |
| 34.9 | 63904 | 2.6 | 13.2 |
| 36.3 | 77597 | 2.5 | 16.0 |
| 36.7 | 83061 | 2.5 | 17.1 |
| 37.7 | 62646 | 2.4 | 12.9 |
| 38.6 | 60200 | 2.3 | 12.4 |
| 39.7 | 61743 | 2.3 | 12.7 |

TABLE 3

Crystallographic Data and Structure Parameter of Crystalline Trandolaprilat Form B

| | |
|---|---|
| Crystallized from | H$_2$O/EtOH/i-PrOH 3.7:1:0.02 |
| Empirical formula | C$_{26}$H$_{42}$N$_2$O$_7$ |
| Formula weight [g mol$^{-1}$] | 494.62 |
| Crystal colour, habit | colorless, prism |
| Crystal dimensions [mm] | 0.15 × 0.17 × 0.30 |
| Temperature [K] | 160(1) |
| Crystal system | orthorhombic |
| Space group | P2$_1$2$_1$2$_1$ (#19) |
| Z | 4 |
| Reflections for cell determination | 2764 |
| 2θ range for cell determination [°] | 4-50 |
| Unit cell parameters    a [Å] | 10.0301(2) |
|              b [Å] | 12.2874(2) |
|              c [Å] | 22.2267(4) |
|              α [°] | 90 |
|              β [°] | 90 |
|              γ [°] | 90 |
|              V [Å$^3$] | 2739.30(9) |
| F(000) | 1072 |
| D$_x$ [g cm$^{-3}$] | 1.199 |
| μ(Mo Kα) [mm$^{-1}$] | 0.0863 |
| Scan type | ø and ω |
| 2θ$_{(max)}$ [°] | 50 |
| Total reflections measured | 33853 |
| Symmetry independent reflections | 2746 |
| R$_{int}$ | 0.057 |
| Reflections with I > 2σ(I) | 2405 |
| Reflections used in refinement | 2743 |
| Parameters refined | 340 |
| Final R(F) [I > 2σ(I) reflections] | 0.0414 |
| wR(F$^2$) (all data) | 0.1116 |

TABLE 3-continued

Crystallographic Data and Structure
Parameter of Crystalline Trandolaprilat Form B

| Weights: | $w = [\sigma^2(F_o^2) + (0.0699P)^2 + 0.3841P]^{-1}$ where $P = (F_o^2 + 2F_c^2)/3$ |
|---|---|
| Goodness of fit | 1.053 |
| Secondary extinction coefficient | 0.015(2) |
| Final $\Delta_{max}/\sigma$ | 0.001 |
| $\Delta\rho$ (max; min) [e Å$^{-3}$] | 0.32; −0.19 |
| $\sigma(d_{C—C})$ [Å] | 0.004-0.006 |

Another method for producing Crystalline Trandolaprilat Form B (from Crystalline Trandolaprilat Form A, Form C and/or Form D) is described hereinbelow under the discussion of Crystalline Trandolaprilat Form E.

Crystalline Trandolaprilat Form C

Crystalline Trandolaprilat Form C is a pseudopolymorphic form of Trandolaprilat that contains a non-stoichiometric amount of water bound in its crystalline structure. The amount of water generally ranges from about 5.4% to about 6.4%. It has the X-ray powder diffraction data shown in Table 4, and the X-Ray powder diffraction pattern shown in FIG. 8.

Crystalline Trandolaprilat Form C can be produced using the "Second Procedure" described hereinabove, and according to Example 3, by acidification of a solution of a salt of formula (3) in water to a pH ranging from about 3.6 to about 4.0 (isoelectric point) followed by crystallization of the Trandolaprilat from the water. An initially formed gum crystallizes slowly by stirring this mixture at a temperature generally ranging from about 20° C. to about 25° C. for a period of time that is preferably at least about 16 hours, whereupon crystalline Trandolaprilat Form C (containing a non-stoichiometric amount of water bound in its crystalline structure) is formed. The crystalline Trandolaprilat Form C can be obtained in a substantially pure crystalline form.

TABLE 4

Powder X-Ray Diffraction Data of Crystalline Trandolaprilat Form C

| Pos. [°2Th.] | Height [cts] | d-spacing [Å] | Rel. Int. [%] |
|---|---|---|---|
| 4.8 | 68 | 18.2 | 0.9 |
| 6.2 | 7234 | 14.2 | 100.0 |
| 8.4 | 88 | 10.5 | 1.2 |
| 10.4 | 911 | 8.5 | 12.6 |
| 11.1 | 368 | 8.0 | 5.1 |
| 11.6 | 247 | 7.6 | 3.4 |
| 12.1 | 128 | 7.3 | 1.8 |
| 12.5 | 1025 | 7.1 | 14.2 |
| 12.8 | 611 | 6.9 | 8.5 |
| 13.3 | 664 | 6.7 | 9.2 |
| 14.0 | 1452 | 6.3 | 20.1 |
| 14.6 | 550 | 6.1 | 7.6 |
| 15.7 | 1664 | 5.7 | 23.0 |
| 16.2 | 636 | 5.5 | 8.8 |
| 16.9 | 393 | 5.2 | 5.4 |
| 18.0 | 899 | 4.9 | 12.4 |
| 18.8 | 1700 | 4.7 | 23.5 |
| 19.3 | 830 | 4.6 | 11.5 |
| 19.5 | 581 | 4.5 | 8.0 |
| 20.1 | 203 | 4.4 | 2.8 |
| 20.8 | 2400 | 4.3 | 33.2 |
| 21.7 | 366 | 4.1 | 5.1 |
| 22.5 | 601 | 4.0 | 8.3 |
| 24.2 | 731 | 3.7 | 10.1 |
| 25.3 | 236 | 3.5 | 3.3 |
| 26.5 | 129 | 3.4 | 1.8 |
| 27.5 | 733 | 3.2 | 10.1 |
| 27.9 | 904 | 3.2 | 12.5 |
| 29.9 | 223 | 3.0 | 3.1 |
| 30.2 | 211 | 3.0 | 2.9 |
| 31.6 | 718 | 2.8 | 9.8 |
| 32.3 | 338 | 2.8 | 4.7 |
| 36.1 | 93 | 2.5 | 1.3 |
| 38.3 | 264 | 2.4 | 3.7 |

The crystalline form D of Trandolaprilat can be obtained by acidification of a solution of compound of formula 3 in water to a pH between 3.6 and 4.0 (isoelectric point) followed by crystallization. The initially formed gum crystallizes slowly by stirring of this mixture at a temperature of 20 to 25° C., and form D having a stoichiometric water content of 4.1% to 4.2% (corresponds to a monohydrate) can be obtained after stirring of this mixture for 3 to 5 d at a temperature between 20 and 25° C.

Crystalline Trandolaprilat Form D

Crystalline Trandolaprilat Form D is a pseudopolymorphic form of Trandolaprilat that contains a stoichiometric amount of water bound in its crystalline structure (1 equivalent of water bound in its crystalline structure (monohydrate)). The amount of water generally ranges from about 4.1% to about 4.2%. It has the X-ray powder diffraction data shown in Table 5, the X-Ray powder diffraction pattern shown in FIG. 9, and the synchrotron profile shown in FIG. 10.

Crystalline Trandolaprilat Form D can be produced using the "Second Procedure" described hereinabove, and according to Example 4, by acidification of a solution of a salt of formula (3) in water to a pH ranging from about 3.6 to about 4.0 (isoelectric point) followed by crystallization of the Trandolaprilat from the water. An initially formed gum crystallizes slowly by stirring this mixture at a temperature generally ranging from about 20° C. to about 25° C. for a period of time that generally ranges from about 3 to about 5 days, whereupon crystalline Trandolaprilat Form D (containing a stoichiometric amount of water bound in its crystalline structure) is formed. The crystalline Trandolaprilat Form D can be obtained in a substantially pure crystalline form.

TABLE 5

Powder X-Ray Diffraction Data of Crystalline Trandolaprilat Form D

| Pos. [°2Th.] | Height [cts] | d-spacing [Å] | Rel. Int. [%] |
|---|---|---|---|
| 6.2 | 50 | 4.3 | 0.4 |
| 8.4 | 1899 | 10.6 | 14.3 |
| 10.5 | 874 | 8.4 | 6.6 |
| 11.5 | 461 | 7.7 | 3.5 |
| 12.0 | 1183 | 7.4 | 8.9 |
| 12.5 | 1748 | 7.1 | 13.2 |
| 13.6 | 1252 | 6.5 | 9.5 |
| 14.4 | 3036 | 6.1 | 22.9 |
| 15.2 | 969 | 5.8 | 7.3 |
| 16.4 | 13246 | 5.4 | 100.0 |
| 17.2 | 8374 | 5.2 | 63.2 |
| 17.5 | 710 | 5.1 | 5.4 |
| 18.8 | 2385 | 4.7 | 18.0 |
| 19.2 | 4452 | 4.6 | 33.6 |
| 19.9 | 3709 | 4.5 | 28.0 |

TABLE 5-continued

Powder X-Ray Diffraction Data of Crystalline Trandolaprilat Form D

| Pos. [°2Th.] | Height [cts] | d-spacing [Å] | Rel. Int. [%] |
|---|---|---|---|
| 20.2 | 634 | 4.4 | 4.8 |
| 21.1 | 549 | 4.2 | 4.1 |
| 22.2 | 4817 | 4.0 | 36.4 |
| 22.5 | 1818 | 4.0 | 13.7 |
| 22.7 | 1501 | 3.9 | 11.3 |
| 23.0 | 933 | 3.9 | 7.1 |
| 23.6 | 1001 | 3.8 | 7.6 |
| 23.9 | 367 | 3.7 | 2.8 |
| 24.6 | 1037 | 3.6 | 7.8 |
| 25.2 | 3240 | 3.5 | 24.5 |
| 25.8 | 659 | 3.5 | 5.0 |
| 26.6 | 948 | 3.4 | 7.2 |
| 27.1 | 1656 | 3.3 | 12.5 |
| 27.5 | 5696 | 3.2 | 43.0 |
| 28.5 | 2383 | 3.1 | 18.0 |
| 29.4 | 2130 | 3.0 | 16.1 |
| 30.0 | 1600 | 3.0 | 12.1 |
| 30.8 | 995 | 2.9 | 7.5 |
| 31.7 | 1694 | 2.8 | 12.8 |
| 32.5 | 1471 | 2.8 | 11.1 |
| 33.3 | 714 | 2.7 | 5.4 |
| 33.7 | 1102 | 2.7 | 8.3 |
| 34.2 | 1568 | 2.6 | 11.8 |
| 34.8 | 1262 | 2.6 | 9.5 |
| 35.3 | 1447 | 2.5 | 10.9 |
| 36.2 | 1249 | 2.5 | 9.4 |
| 37.7 | 1121 | 2.4 | 8.5 |
| 38.5 | 1619 | 2.3 | 12.2 |
| 39.0 | 1491 | 2.3 | 11.3 |

Preparation of Crystalline Trandolaprilat Form C and Its Transformation to Crystalline Trandolaprilat Form D Trandolaprilat obtained from the "Second Procedure" is slurried in water according to Example 4, Procedure B. Table 6 shows the transformation of the initially formed Trandolaprilat Crystalline Form C (water content: 5.4-6.4%) to the monohydrate (Crystalline Trandolaprilat Form D, water content: 4.2%). The conversion is followed by regular in process controls (filtration of a sample of the slurry) and determination of the water content of the sample after drying of the wet product by, for example, dry in vacuo. It is presently preferred to dry at a temperature not greater than about 60° C.

TABLE 6

Formation of Monohydrate

| | Sample Number | | | |
|---|---|---|---|---|
| | 1 | 2 | 3 | 4 |
| Stirring Time (hours) | 22 | 50 | 73 | 97 |
| Water Content (%) | 5.4-6.4 | 5.9 | 4.5 | 4.2 |

Crystalline Trandolaprilat Form E

Crystalline Trandolaprilat Form E is a polymorphic non-solvate form of Trandolaprilat. It has the X-ray powder diffraction data shown in Table 8 and the X-Ray powder diffraction pattern shown in FIG. 11.

Crystalline Trandolaprilat Form E, and a method for producing it, were developed in response to a need to produce Trandolaprilat that meets certain specifications: (i) a water content that is ≦1.0%; (ii) a content of residual solvent according to the limits described in the ICH Guideline (which may be obtained at www.ich.org); and (iii) an amount of the degradation impurity "Trandolaprilat diketopiperazine" that is ≦1.0%, as measured by HPLC. Crystalline Trandolaprilat Form E has each of these characteristics.

As is discussed above, it was found that Trandolaprilat forms different pseudopolymorphic forms containing stoichiometric or non-stoichiometric amounts of water and/or other solvents when it is crystallized from hydroxylic solvents, such as water, alcohols or mixtures thereof. The final amount of solvent in Trandolaprilat can depend upon: (i) the solvent composition; and (ii) conditions chosen for crystallization.

Moreover, when any one of the isolated crystalline pseudopolymorphic forms, such as Form A, Form B, Form C or Form D, was treated with a hydroxylic solvent, such as alcohols or water, or a mixture thereof, an exchange of the crystal bound solvent was observed (a transformation of one pseudopolymorphic form into another pseudopolymorphic form). For instance, crystal bound butanol in Crystalline Trandolaprilat Form A, or water in Crystalline Trandolaprilat Form D, can be removed by ethanol when these crystalline forms are slurried in ethanol. This result shows that Trandolaprilat has a high tendency to form different pseudopolymorphic forms when crystallized from hydroxylic solvents, such as alcohols and/or water, which can result in an amount of these solvents being present in the final product that exceeds the required specification.

A discovery of one or more stable processes for removing excess solvent or water from a crystalline pseudopolymorphic form of Trandolaprilat, however, resulted in a variety of different difficulties. It was found that if Trandolaprilat existing as any one of the above-described crystalline forms, or mixtures thereof, was slurried or recrystallized from one or more non-hydroxylic solvents, such as toluene, MTBE, methylethylketone, acetone, ethyl acetate, THF or the like, or mixtures thereof, then disadvantageously degradation of the Trandolaprilat product to the impurity (degradation product) "Trandolaprilat diketopiperazine" was observed (i.e. poor results were obtained). The rate of degradation was found to depend upon both: (i) temperature employed; and (ii) type of solvent employed. For example, crystalline Trandolaprilat dissolved in THF showed a degradation of at least 0.2% per hour at room temperature, and the formation of this degradation product was almost complete within a few hours when this solution was heated at reflux temperature. Furthermore, crystallization and precipitation from non-hydroxylic solvents often provided a resin that could only be difficultly handled.

It was surprisingly and unexpectedly discovered that the Trandolaprilat disolvate containing ethanol in the crystal unit (crystalline Trandolaprilat Form B—pseudopolymorphic form) could be easily transformed under mild conditions to the non-solvate form of Trandolaprilat (crystalline Trandolaprilat Form E—polymorphic Form) if it is handled under specific drying conditions (discussed in Table 7 below). Only a low amount of the degradation product Trandolaprilat diketopiperazine was observed, and the solvent (ethanol) could be removed almost completely, resulting in a product that meets the above-described specifications. The rate of the transformation was found to depend upon: (i) particle size of the crystalline Trandolaprilat Form B; (ii) drying temperature; (iii) vacuo conditions; and (iv) drying time. The crystalline Trandolaprilat Form B is preferably dried at a temperature ranging from about 20° C. to about 60° C., and preferably ranging from about 40° C. to about 60° C., optionally in vacuo. A size reduction of crystalline Trandolaprilat Form B by, for example milling or grinding.

Further, crystalline Trandolaprilat Forms A, C or D, or mixtures thereof, can typically be transformed by a slurry in ethanol into substantially pure crystalline Trandolaprilat Form B, whereupon the crystal bound solvent can then be removed using ethanol, as is described in the preceding paragraph. The temperature for the slurry generally ranges from about 0° C. to reflux temperature, and preferably ranges from about 10° C. to about 60° C., and most preferably ranges from about 20° C. to about 45° C. A period of time ranging from about 10 to about 15 hours is generally sufficient for the transformation of the crystalline forms at a temperature ranging from about 20° C. to about 45° C. A shorter stirring time at lower temperatures can disadvantageously cause an incomplete conversion. In contrast, a prolonged stirring time at higher temperatures can disadvantageously produce the degradation product "Trandolaprilat diketopiperazine" in larger quantities. The Crystalline Trandolaprilat Form B that is obtained can then be dried in the manner described hereinabove and in Table 7 to provide Crystalline Trandolaprilat Form E.

The results of experiments performed to transform crystalline Trandolaprilat Form B into crystalline Trandolaprilat Form E under different drying conditions (to dry wet crystalline Trandolaprilat Form B obtained by a slurry in ethanol) are summarized in Table 7 below. The results in Table 7 show that the higher the temperature is, or the lower the vacuum for a certain drying condition is, the easier it generally is to transform crystalline Trandolaprilat Form B into crystalline Trandolaprilat Form E (the non-solvate) with an almost complete removal of ethanol. However, a prolongation of the drying time at higher temperatures can also cause the formation of higher amounts of the degradation product Trandolaprilat diketopiperazine.

TABLE 8-continued

Powder X-Ray Diffraction Data of Crystalline Trandolaprilat Form E

| Pos. [°2Th.] | Height [cts] | d-spacing [Å] | Rel. Int. [%] |
|---|---|---|---|
| 12.2 | 393 | 7.3 | 7.3 |
| 12.9 | 592 | 6.9 | 11.0 |
| 14.9 | 1214 | 6.0 | 22.6 |
| 17.4 | 5380 | 5.1 | 100.0 |
| 17.7 | 2818 | 5.0 | 52.4 |
| 19.2 | 963 | 4.6 | 17.9 |
| 20.2 | 1049 | 4.4 | 19.5 |
| 21.0 | 1838 | 4.2 | 34.2 |
| 22.1 | 403 | 4.0 | 7.5 |
| 23.1 | 759 | 3.9 | 14.1 |
| 24.8 | 998 | 3.6 | 18.6 |
| 26.1 | 679 | 3.4 | 12.6 |
| 28.4 | 2449 | 3.1 | 45.5 |
| 31.1 | 757 | 2.9 | 14.1 |
| 31.9 | 463 | 2.8 | 8.6 |
| 34.5 | 325 | 2.6 | 6.0 |
| 35.5 | 361 | 2.5 | 6.7 |
| 37.2 | 539 | 2.4 | 10.0 |

Figure 12:
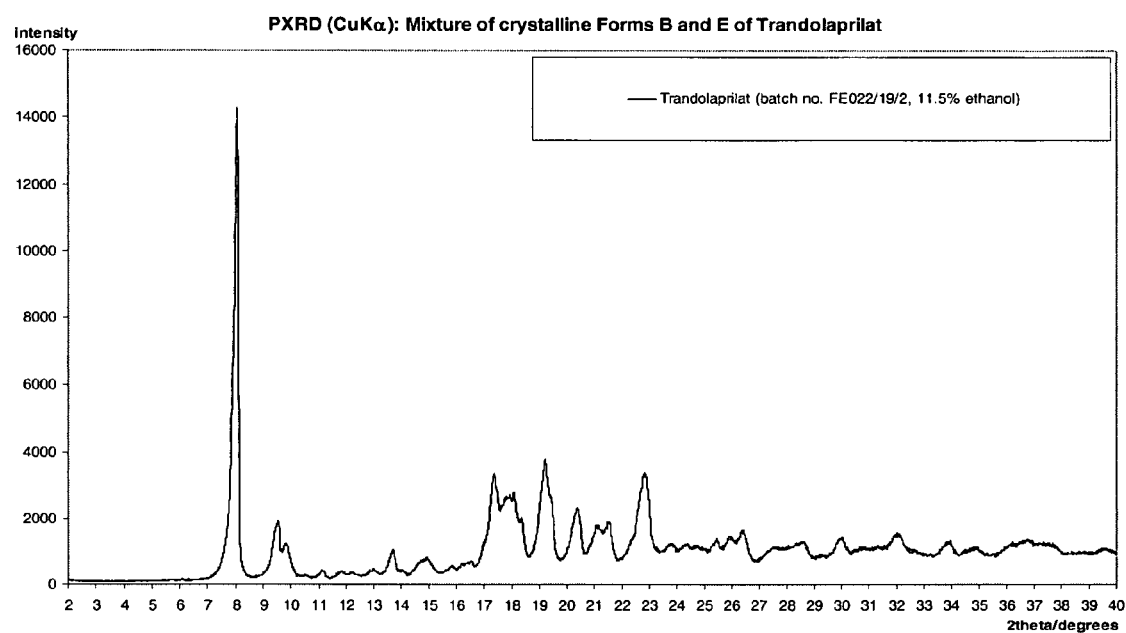
FIG. 12 is an X-ray powder diffraction pattern of a mixture of crystalline Trandolaprilat Form B and crystalline Trandolaprilat Form E.

FIG. 12 shows the X-Ray powder diffraction pattern of a mixture of crystalline Trandolaprilat Form B and crystalline Trandolaprilat Form E that was obtained by a slurry of crystalline Trandolaprilat Form B in ethanol and after drying of the wet product at about 40° C. for about 15 hours in vacuo (from about 1 to about 5 mbar).

Storage Stability of Crystalline Forms of Trandolaprilat

Table 9 provides storage stabilities of different crystalline forms of Trandolapril. This table shows that, in comparison with other forms, Trandolaprilat as a non-solvate (crystalline Trandolaprilat Form E) appears to have a greater tendency to decompose to the corresponding degradation product Trandolaprilat Diketopiperazine, with more decomposition being associated with a higher storage temperature. The tendency of crystalline Trandolaprilat Form C (containing a non-stoichiometric amount of water bound to its crystalline structure) and crystalline Trandolaprilat Form B (containing 2 equivalents of ethanol bound to its crystalline structure) to decompose to

TABLE 7

Drying Conditions Employed in Experiments to Transform Wet Crystalline Trandolaprilat Form B into Crystalline Trandolaprilat Form E

| | | | In process control | | | | Final product | | | | |
|---|---|---|---|---|---|---|---|---|---|---|---|
| Batch Number | Drying Temperature [° C.] | Drying Pressure [mbar] | Drying Time [hours] | HPLC Purity [%] | Trandolaprilat Diketo-piperazine [HPLC-%] | EtOH Content [%] | Total Drying Time [hours] | HPLC Purity [%] | Trandolaprilat Diketo-piperazine [HPLC-%] | EtOH Content [%] | $H_2O$ Content |
| FE022/48/B | 40 | 1-5 | 4 | 100 | — | 13.6 | 15 | 99.92 | 0.08 | 10.3 | 0.61 |
| FE022/48/C | 50 | 1-5 | 4 | 99.93 | 0.07 | 8.67 | 15 | 99.71 | 0.29 | 0.18 | 0.74 |
| FE022/48/D | 60 | 1-5 | 4 | 99.72 | 0.27 | 0.08 | 15 | 99.2 | 0.75 | 0.02 | 0.87 |
| FE022/48/E | 40 | <1 | n.d. | n.d. | n.d. | n.d. | 18 | 99.81 | 0.19 | 0.051 | 0.74 |
| FE022/56/3 | 40 | <1 | n.d. | n.d. | n.d. | n.d. | 92 | 99.63 | 0.32 | 0.086 | 0.29 |

TABLE 8

Powder X-Ray Diffraction Data of Crystalline Trandolaprilat Form E

| Pos. [°2Th.] | Height [cts] | d-spacing [Å] | Rel. Int. [%] |
|---|---|---|---|
| 9.4 | 1501 | 9.4 | 27.9 |
| 9.8 | 2865 | 9.0 | 53.3 | the corresponding degradation product appears to be significantly lower, but degradation could still be determined. In contrast, crystalline Trandolaprilat Form A (containing 2 equivalents of butanol in the crystal unit) and crystalline Trandolaprilat Form D (containing one equivalent of water in the crystal unit) stabilize Trandolaprilat dramatically, with only a very low quantity of the degradation product being observed after four months of storage at room temperature.

TABLE 9

Storage Stabilities of Different Crystalline Forms of Trandolapril

| Crystalline Form of Trandolaprilat | Amount of Trandolaprilat Diketopiperazine after Isolation and Drying of the Wet Product [%, by HPLC] | Storage Temperature | Storage Time [Months] | Amount of Trandolaprilat Diketopiperazine after Storage [% by HPLC] |
|---|---|---|---|---|
| Form A | Not Detected | 20-25 | 4 | 0.02 |
| Form B[1] | Not Detected | 20-25 | 4 | 0.20 |
| Form C | Not Detected | 20-25 | 4 | 0.26 |
| Form D | Not Detected | 20-25 | 4 | 0.03 |
| Form E | 0.34 | 4-8 | 3 | 0.75 |
| Form E | 0.19 | 20-25 | 3 | 0.92 |

[1]Crystals obtained according to Example 2 which were stored in a sealed vial.

Pharmaceutical Compositions

The present invention also provides pharmaceutical compositions comprising a therapeutically effective amount of at least one Trandolaprilat compound of the invention (as an active ingredient) and one or more pharmaceutically acceptable carriers. Optionally, the pharmaceutical compositions may include one or more other compounds, drugs or materials that are compatible with the Trandolaprilat compound(s) and carrier(s), which may readily be determined by those of ordinary skill in the art, including, but not limited to, coloring agents, release agents, coating agents, sweetening and/or flavoring agents, adhesive agents, perfumes, preservatives and/or antioxidants.

In a preferred embodiment, the pharmaceutical compositions of the invention include crystalline Trandolaprilat Form A, crystalline Trandolaprilat Form B, crystalline Trandolaprilat Form C, crystalline Trandolaprilat Form D or crystalline Trandolaprilat Form E, or any combination thereof.

In another preferred embodiment, the pharmaceutical compositions of the invention include a Trandolaprilat compound in a crystalline form comprising a structure of formula (4) wherein R is a C1-C4 alkyl, and wherein the amount of alcohol present in the pharmaceutical composition does not exceed about 5,000 ppm, with the proviso that, if R is a C1 alkyl, the amount of alcohol present in the pharmaceutical composition does not exceed about 3,000 ppm.

In yet another preferred embodiment, the pharmaceutical compositions of the invention include a Trandolaprilat compound in a crystalline form comprising a structure of formula (4) wherein n=0, and wherein the amount of water that is present in the pharmaceutical composition does not exceed about 1.0%.

The pharmaceutical compositions of the invention may, for example, be specifically formulated for an oral administration in a solid or liquid form or for a transdermal administration.

Formulations of the invention suitable for an oral administration may be in the form of capsules, cachets, pill, tablets, lozenges, powders, granules, as a solution or suspension in an aqueous or non-aqueous liquid, as an emulsion, as an elixir or syrup or the like. Solid dosage forms of the pharmaceutical compositions of the invention may, optionally, be scored or coated with one or more enteric or other coatings that are well known in the pharmaceutical-formulating art. They may also be formulated so as to provide a slow or controlled release of the active ingredient contained therein.

Formulations of the invention suitable for a transdermal administration may be in the form of powders, sprays, ointments, pastes, creams, lotions, gels, solutions and patches. Transdermal patches may have an added advantage of providing a controlled delivery of a Trandolaprilat compound of the invention to the body.

Methods for preparing the pharmaceutical compositions of the present invention generally include the step of bringing into association one or more Trandolaprilat compounds of the invention with one or more carrier materials and, optionally, with one or more accessory ingredients.

For a preparation of oral dosage forms, the pharmaceutical compositions of the present invention may be prepared, for example, by uniformly and intimately bringing into association one or more Trandolaprilat compounds with one or more liquid or finely divided solid carriers and then, if necessary or desired, shaping (with compression, molding or the like) or encapsulating the product. Methods for producing pharmaceutical formulations that are suitable for an oral administration by humans and/or animals are well known by those of skill in the art and are described, for example, in "Pharmaceutical Capsules" (ISBN 0-85369-568-7, Pharmaceutical Press, 2004) and in "Handbook of Pharmaceutical Manufacturing Formulations" (ISBN 0-84931-7479, CRC Press, 1999).

Transdermal dosage forms can be made, for example, by dissolving or dispersing one or more Trandolaprilat compounds in a proper medium. Absorption enhancers can also be used to increase the flux of the compound across the skin. The rate of such flux can be controlled, for example, by providing a rate controlling membrane or dispersing the compound in a polymer matrix or gel. Methods for producing transdermal patches for therapeutic uses are well known in the pharmaceutical industry. Such methods are, for example, described in published patent application No. U.S. 2004/0052835, in U.S. Pat. Nos. 5,290,561 and 6,303,141, and in Russell O. Potts and Richard H. Guy, "Mechanisms of Transdermal Drug Delivery, Drugs and Pharmaceutical Sciences: a Series of Textbooks and Monographs" (ISBN 0-8247-9863-5, 1997) and Kenneth A. Walters, "Dermatological and Transdermal Formulations, Drugs and the Pharmaceutical Sciences: a Series of Textbooks and Monographs" (ISBN 0-8247-9889-9, 2002).

The pharmaceutical compositions of the present invention would generally be used under the guidance of a physician, with the appropriate form of administration and dosage being suitably selected by methods that are consistent with conventional medical, veterinary and pharmaceutical practices.

Regardless of the route of administration selected, the Trandolaprilat compounds and pharmaceutical compositions of the present invention may be formulated into pharmaceutically-acceptable dosage forms by conventional methods known by those of skill in the art.

Actual dosage levels of the active ingredient(s) employed in the pharmaceutical compositions of the invention may be varied so as to obtain an amount of the active ingredient that is effective for achieving a desired therapeutic response for a particular patient, composition and mode of administration, without being toxic to the patient.

The selected dosage level may depend upon a variety of factors known by those of skill in the art, such as the activity of the particular Trandolaprilat compound(s) being employed, or salt thereof, the route of administration, the time of administration, the rate of excretion of the particular Trandolaprilat compound(s) being employed, the severity of the medical condition being treated, the duration of the treatment, other drugs, compounds and/or materials being employed in combination with the Trandolaprilat compound(s), the age, sex, weight, condition, general health and prior medical history of the patient being treated, and like factors that are well known in the medical, veterinarian and pharmaceutical arts.

A physician or veterinarian having ordinary skill in the art can readily determine and prescribe the effective amount of a pharmaceutical composition of the present invention that is required to treat a particular patient's medical problem. For example, the physician or veterinarian could start a dose of a Trandolaprilat compound of the invention employed in the pharmaceutical composition at a level that is lower than that required to achieve a desired therapeutic effect and gradually increase the dosage until the desired effect is achieved.

In general, a suitable daily dose of a Trandolaprilat compound of the invention, or of a pharmaceutical composition that includes one or more Trandolaprilat compounds of the invention, will be that amount of the Trandolaprilat compound that is the lowest dose that is effective for producing a desired therapeutic effect, which will generally depend upon one or more of the factors discussed above. Such dosage may be determined by an attending physician or veterinarian within the scope of sound medical or veterinary judgment.

If desired, the effective daily dosage of the active Trandolaprilat compound may be administered as two, three, four, five, six or more sub-doses administered separately at appropriate intervals throughout the day, optionally, in unit dosage forms.

Methods of Treatment

The Trandolaprilat compounds and pharmaceutical compositions of the present invention are useful for producing an antihypertensive effect in human beings and animals. The present invention, thus, also provides a method for treating high blood pressure, cardiac insufficiency or other medical conditions related to hypertension comprising administering to a subject in need of such treatment an effective amount of a pharmaceutical composition of the invention. A physician or veterinarian of ordinary skill in the art can readily determine whether or not a subject is in need of such treatment.

In a preferred embodiment, the pharmaceutical composition employed in the methods of the invention includes crystalline Trandolaprilat Form A, crystalline Trandolaprilat Form B, crystalline Trandolaprilat Form C, crystalline Trandolaprilat Form D, crystalline Trandolaprilat Form E, or any combination thereof.

The following examples describe and illustrate crystalline forms of Trandolaprilat, and methods within the present invention, and are intended to be merely illustrative of the present invention, and not limiting thereof in either scope or spirit. Those of skill in the art will readily understand that variations of certain of the conditions and/or steps employed in the procedures described in the examples can be used to prepare these crystalline forms. All yields that have been calculated were corrected by assay.

EXAMPLE 1

Preparation of Crystalline Trandolaprilat Form A

Crystalline Trandolaprilat Form A was prepared in accordance with the First Procedure described hereinabove.

A solution of NaOH (6.5 g, 153.6 mmol; assay=94.52%), water (157 ml), ethanol (157 ml, technical grade, contains ~5% 2-propanol) and Trandolapril (31.5 g, 72.94 mmol; assay=99.7%) was stirred at an internal temperature ranging from about 20° C. to about 25° C. for 15 hours. After an in-process control showed an almost complete saponification (by HPLC), the clear solution was concentrated in vacuo to an amount of 167.05 g, and n-butanol (160 ml) was added to the concentrated product. This mixture was heated to an internal temperature ranging from about 60° C. to about 70° C., and 2N aqueous hydrochloric acid was added (150.4 mmol), whereupon the pH dropped down from 12.09 to 3.66. The organic layer was separated at an internal temperature of 66° C., and the aqueous layer was extracted again with n-butanol (80 ml) at an internal temperature of 65° C. The combined organic layers were washed twice with water (each 40 ml) at an internal temperature ranging from about 63° C. to about 65° C. The organic layer then obtained (total amount 306.4 g) was concentrated in vacuo at a temperature ranging from about 50° C. to about 60° C., whereupon after concentration to an amount of 190 g a white solid precipitated. This suspension was further concentrated in vacuo to an amount of 75.1 g, and 80 ml MTBE was added to complete the precipitation. The suspension was stirred at an internal temperature ranging from about 20° C. to about 25° C. for 3.5 hours. After filtration, the wet product was washed twice with MTBE (each 80 ml) and dried in vacuo for 15 hours at 40° C. to give Trandolaprilat as disolvate with n-butanol (yield: 36.51 g, 66.67 mmol, 91.4%; assay (0.1N HClO$_4$)=73.5%; HPLC purity=100%).

EXAMPLE 2

Isolation of Trandolaprilat from The Reaction Mixture and Crystallization of Form B as Single Crystals Trandolaprilat was crystallized and isolated in accordance with the Second Procedure described hereinabove.

A solution of NaOH (0.96 g, 22.68 mmol; assay=94.52%), water (22 ml), ethanol (22 ml, technical grade, contains ~5% 2-propanol) and Trandolapril (4.5 g, 10.42 mmol; assay=99.7%) was stirred at an internal temperature ranging from about 20° C. to about 25° C. for 19 hours. After an in process control showed an almost complete saponification (by HPLC), the clear solution was acidified at a temperature ranging from about 20° C. to about 25° C. with 2N aqueous hydrochloric acid to a pH of 3.8 (22.8 mmol; the solution was seeded during acidification and the crystallization started at pH=4.6). The suspension was stirred at a temperature ranging from about 20° C. to about 25° C. (the stirring time in this case after pH adjustment was 47 hours and the pH was adjusted from 3.71 to 3.82 by an addition of 1 drop of 2N aqueous NaOH solution; generally a maximum stirring time of 5 to 6 hours at this pH is sufficient) and then filtered off. The wet product was washed with water (30 ml) and dried in vacuo (1-5 mbar) for 15 hours at 40° C. to give Trandolaprilat (yield: 4.0 g, 9.06 mmol, 86.9%; assay=91.15%; water content: 1.02-

1.12%, ethanol content: 7.52-8.44%, 2-propanol content: 0.26-0.29, chloride content=not detected).

As is discussed hereinabove, the content of solvents in the final product can vary depending on the conditions employed.

Crystallization of Trandolaprilat Crystalline Form B for X-ray Measurement

The combined filtrates were stored for 12 days at a temperature ranging from about 20° C. to about 25° C., whereupon additional Trandolaprilat crystallized slowly. The crystals were collected and dried at 30° C. in vacuo for 14.5 hours. X-ray measurements showed the presence of a pure Trandolapril disolvate with 2 equivalents ethanol.

Note: General Seeding Procedure

The acidification of the mixture with 2N aqueous HCl is stopped after a pH ranging from about 4.5 to about 5.0 is reached. The mixture is then seeded using Trandolaprilat crystalline Form B and stirred at a temperature ranging from about 20° C. to about 25° C. until a crystallization can be observed clearly (within a period of from about 10 to about 15 minutes; the pH rises during the stirring and crystallization period). Afterwards, the addition of the 2N aqueous HCl is continued (dropwise) until the pH of the isoelectric point is reached.

EXAMPLE 3

Preparation of Crystalline Trandolaprilat Form C

Crystalline Trandolaprilat Form C was prepared in accordance with the Second Procedure described hereinabove.

A solution of NaOH (1.84 g, 43.48 mmol; assay=94.52%), water (45 ml), ethanol (45 ml, technical grade, contains ~5% 2-propanol) and Trandolapril (9.0 g, 20.78 mmol; assay=99.4%) was stirred at an internal temperature ranging from about 20° C. to about 25° C. for 14 hours. After an in process control showed an almost complete saponification (by HPLC), the reaction mixture was concentrated in vacuo to an amount of 64.64 g One half of the concentrated reaction mixture was used and the pH was adjusted to 3.8 by an addition of 2N aqueous hydrochloric acid (21.61 mmol) and a few drops of 2N aqueous NaOH solution. Initially during acidification, a sticky flocculent precipitation at a pH of 6 was observed, and upon further acidification a suspension containing a fine white solid was formed. The suspension was stirred at a temperature ranging from about 20° C. to about 25° C. for 16 hours and filtered off. The wet product was washed with water (30 ml) and acetone (30 ml) and dried in vacuo (1-5 mbar), 24 hours at 40° C. and 24 hours at room temperature) to give crystalline Trandolaprilat Form C (yield: 3.18 g, 7.45 mmol, 71.7% (extrapolated); assay (0.1N HClO$_4$)=94.35%; HPLC purity=100%; water content: 5.67%, chloride content=0.16%).

EXAMPLE 4

Preparation of Crystalline Trandolaprilat Form D

Crystalline Trandolaprilat Form D was prepared in two different manners, as is described below (Procedure A and Procedure B).

Procedure A

In Procedure A, crystalline Trandolaprilat Form D was prepared in accordance with the Second Procedure described hereinabove.

A solution of NaOH (0.92 g, 21.74 mmol; assay=94.52%), water (22 ml), ethanol (22 ml, technical grade, contains ~5% 2-propanol) and Trandolapril (4.5 g, 10.39 mmol; assay=99.4%) was stirred at an internal temperature ranging from about 20° C. to about 25° C. for 19 hours. After an in process control showed an almost complete saponification (by HPLC), the reaction mixture was concentrated in vacuo to an amount of 24.42 g. This clear solution (pH=13) was slowly added to a mixture of 2N aqueous hydrochloric acid (25.22 mmol) and water (12 ml) at a temperature ranging from about 20° C. to about 25° C. within a period of 1 hour. During the addition, a sticky flocculent precipitation was observed. Afterwards, the pH of the mixture was adjusted from 2.74 to 3.84 by an addition of a few drops of 2N aqueous NaOH solution, and the mixture was stirred at a temperature ranging from about 20° C. to about 25° C. for 4 days. The suspension was then filtered off, the wet product was washed with water (15 ml) and dried in vacuo (1-5 mbar) for 15 hours at 40° C. to give Trandolaprilat in the crystalline Form D (yield: 4.07 g, 9.54 mmol, 91.8%; assay (0.1N HClO$_4$)=96%; HPLC purity: 99.82%; water content: 4.13%, chloride content=0.15%).

Procedure B

A solution of NaOH (6.70 g, 158.3 mmol; assay=94.52%), water (98 ml), ethanol (98 ml, technical grade, contains ~5% 2-propanol) and Trandolapril (31.5 g, 72.94 mmol; assay=99.7%) was stirred at an internal temperature ranging from about 20° C. to about 25° C. for 21 hours. After an in process control showed an almost complete saponification (by HPLC), the clear solution was acidified at a temperature ranging from about 20° C. to about 25° C. with 2N aqueous hydrochloric acid to a pH=3.8 (159 mmol; the addition of 2N aqueous HCl was stopped at pH=4.67 and the solution was seeded whereupon the crystallization started slowly; after approximately 10 minutes the addition of 2N aqueous HCl was continued). The suspension was stirred for 22 hours at a temperature ranging from about 20 to about 25° C. and then filtered off to give 42.12 g of wet product.

2.7 g of the wet product were dried in vacuo (1-5 mbar) for 15 hours at 40° C. to give Trandolaprilat (yield: 1.84 g, 4.31 mmol, 5.9%; assay=94.18%; water content: 1.42-1.47%, ethanol content: 4.17-4.26%, 2-propanol content: 0.19, chloride content=not detected).

A slurry of the remaining wet product in water (230 ml) was heated to an internal temperature of 55° C., then cooled to an internal temperature ranging from about 20° C. to about 25° C. and stirred at this temperature for a total of 4 days. In periodical intervals samples (in process controls) were taken from the suspension to determine the water content.

After 21.5 hours, a sample was taken, filtered off, washed with water (10 ml) and dried in vacuo (1-5 mbar) for 15 hours at 40° C. to give Trandolaprilat (yield: 1.2 g, 2.81 mmol, 3.86%; assay=94.4%; water content: 5.35-6.4%, ethanol content: not detected, 2-propanol content: not detected, chloride content=not detected).

After an additional 28 hours, a sample was taken, filtered off, washed with water (10 ml) and dried in vacuo (1-5 mbar) for 15 hours at 40° C. to give Trandolaprilat (yield: 1.04 g, 2.43 mmol, 3.33%; water content: 5.92%).

After an additional 23 hours, a sample was taken, filtered off, washed with water (10 ml) and dried in vacuo (1-5 mbar) for 15 hours at 40° C. to give Trandolaprilat (yield: 1.48 g, 3.51 mmol, 4.81%; water content: 4.52%).

After an additional 24 hours, the remaining suspension was filtered off and the wet product was washed with water (100 ml) and dried in vacuo (1-5 mbar) for 18 hours at 40° C. to give Trandolaprilat (yield: 21.04 g, 50.04 mmol, 68.61%, overall yield: 86%; assay (0.1N HClO$_4$)=95.73%; HPLC purity: 99.98%; water content: 4.18%, ethanol content: not detected, 2-propanol content: not detected, chloride content: not detected).

EXAMPLE 5

Methods for Preparation of Crystalline Trandolaprilat Form B and Its Transformation to Crystalline Form E Crystallization and Isolation of Trandolapril Wet Product from The Saponification Mixture and X-Ray Powder Diffraction (PXRD) Investigations A solution of NaOH (10.8 g, 255 mmol; assay=94.5%), water (158 ml), ethanol (158 ml) and Trandolapril (50 g, 115 mmol; assay=99.4%) was stirred at an internal temperature ranging from about 20° C. to about 25° C. for 16.5 hours. After an in process control showed an almost complete saponification (by HPLC), the pH of the clear solution was adjusted to 3.8 by addition of 2N aqueous hydrochloric acid at a temperature ranging from about 20° C. to about 25° C. (The solution was seeded at pH=4.6 according to the general seeding procedure (see Example 2); in this case within 10 minutes the crystallization started and the pH arose to 5.55 during the crystallization, whereupon the acidification was continued until pH=3.8 was reached). After five minutes stirring at pH=3.8, a sample of the suspension was taken for analytical purpose. (The filtered sample was washed with approx. 5 ml EtOH/water (1/1, v/v) to give 1.4 g of a first wet product; an X-ray powder diffraction (PXRD) measurement of this sample showed the presence of pure Trandolapril polymorphic Form B).

The remaining suspension was stirred at a temperature ranging from about 20° C. to about 25° C. for 5 hours, and then filtered off, and the wet product was washed with water (160 ml) and ethanol (160 ml) to give 63.5 g of a second wet product containing Trandolaprilat as pure crystalline Form B.

Investigations Using the Second Wet Product:

INVESTIGATION EXAMPLE 1

7.6 g of the second wet product were dried in a crystallizing dish at room temperature (normal pressure) and in a slight airstream for 18 hours to give Trandolaprilat predominantly as crystalline Form B contaminated with low amounts of Form E (yield: 7.4 g; assay (0.1N $HClO_4$)=81.91%; HPLC purity: 99.96%, Trandolaprilat diketopiperazine: not detected; water content: 0.55%, ethanol content: 17.9%). Note: Shorter drying time at this condition may avoid the transformation, while longer drying time at the same temperature may increase the amount of Form E up to the point where the transformation is complete (see also investigation Example 7).

Generally the rate of the transformation of Form B to Form E depends on drying temperature, vacuum and particle size. The transformation can be accelerated either by grinding or milling of the wet product and/or drying in vacuum at the same or higher temperatures as, for example, is described in investigation Examples 2 and 3 or Table 7. The transformation time on lager scale may be prolonged depending on the drying method and/or equipment used (e.g. thickness of the substance layers when tray dryers are used).

INVESTIGATION EXAMPLE 2

5 g of the second wet product were dried in vacuo at 50° C. (1-5 mbar) for 15 hours to give Trandolaprilat as crystalline Form E (yield: 3.8 g; assay (0.1N $HClO_4$)=99.41%; HPLC purity: 99.57%, Trandolaprilat diketopiperazine: 0.40%; water content: 0.34%, ethanol content: 0.10%).

INVESTIGATION EXAMPLE 3

5 g of the second wet product were dried in vacuo at 50° C. (<1 mbar) for 25 hours to give Trandolaprilat as crystalline Form E (yield: 3.7 g; assay (0.1N $HClO_4$)=98.9%; HPLC purity: 99.48%, Trandolaprilat diketopiperazine: 0.51%; water content: 0.27%, ethanol content: 0.09%).

INVESTIGATION EXAMPLE 4

A suspension of 32.4 g of the second wet product in ethanol (200 ml) was stirred at a temperature of about 40° C. for 16 hours, and then at a temperature ranging from about 20° C. to about 25° C. for 2 hours. After filtration, the wet product was washed with ethanol (80 ml) to give 31.4 g of a third wet product as pure crystalline Form B.

Investigations Using the Third Wet Product:

INVESTIGATION EXAMPLE 5

The second half of the third wet product was dried in a crystallizing dish at room temperature (normal pressure) and in a slight airstream for 21.5 hours to give Trandolaprilat as crystalline Form B (yield: 13.6 g; assay (0.1N $HClO_4$) =81.57%; HPLC purity: 99.97%, Trandolaprilat diketopiperazine: not detected; water content: 0.56%, ethanol content: 18.49%). Note: see investigation Example 1.

INVESTIGATION EXAMPLE 6

Approximately one half of the third wet product was dried in vacuo (<1 mbar) at 50° C. for 21.5 hours to give Trandolaprilat as crystalline Form E (yield: 11.2 g; assay (0.1N $HClO_4$)=99.04%; HPLC purity: 99.52%, Trandolaprilat diketopiperazine: 0.45%; water content: 0.30%, ethanol content: 0.06%).

INVESTIGATION EXAMPLE 7

Figure 15:
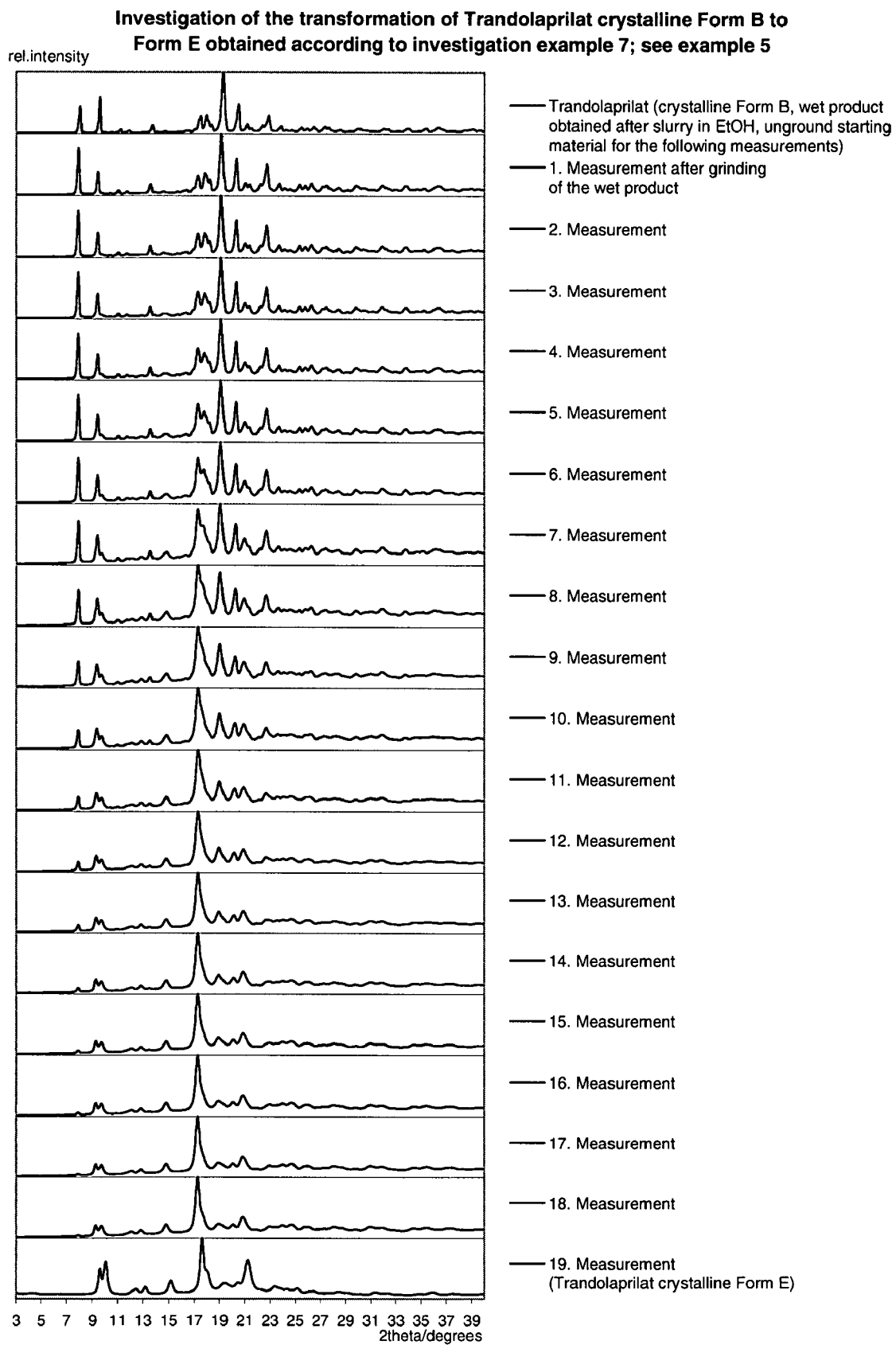
FIG. 15 shows the conversion of a ground sample of Trandolaprilat crystalline Form B to Form E investigated by successive X-ray powder diffraction (PXRD) measurements.
Figure 16:
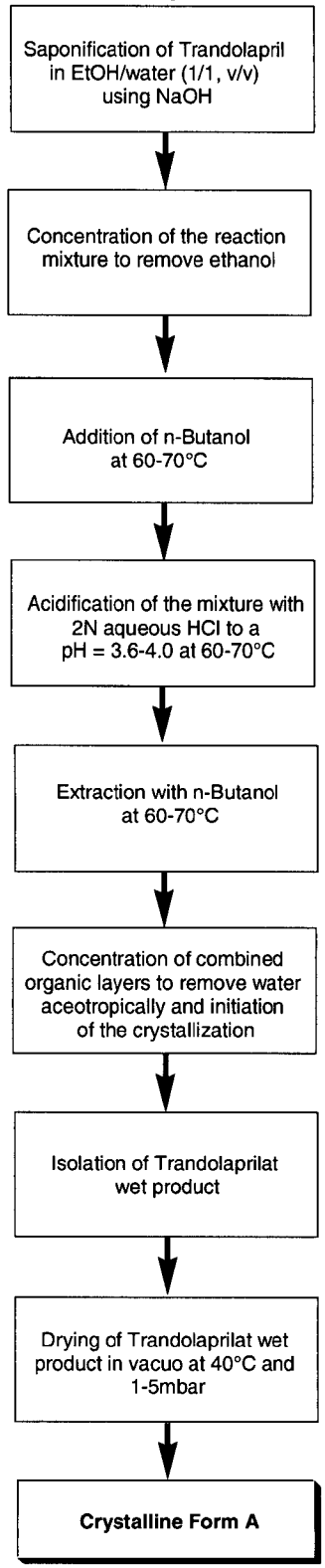
FIG. 16 is an overview showing the method for preparing Trandolaprilat crystalline Form A.
Figure 17:
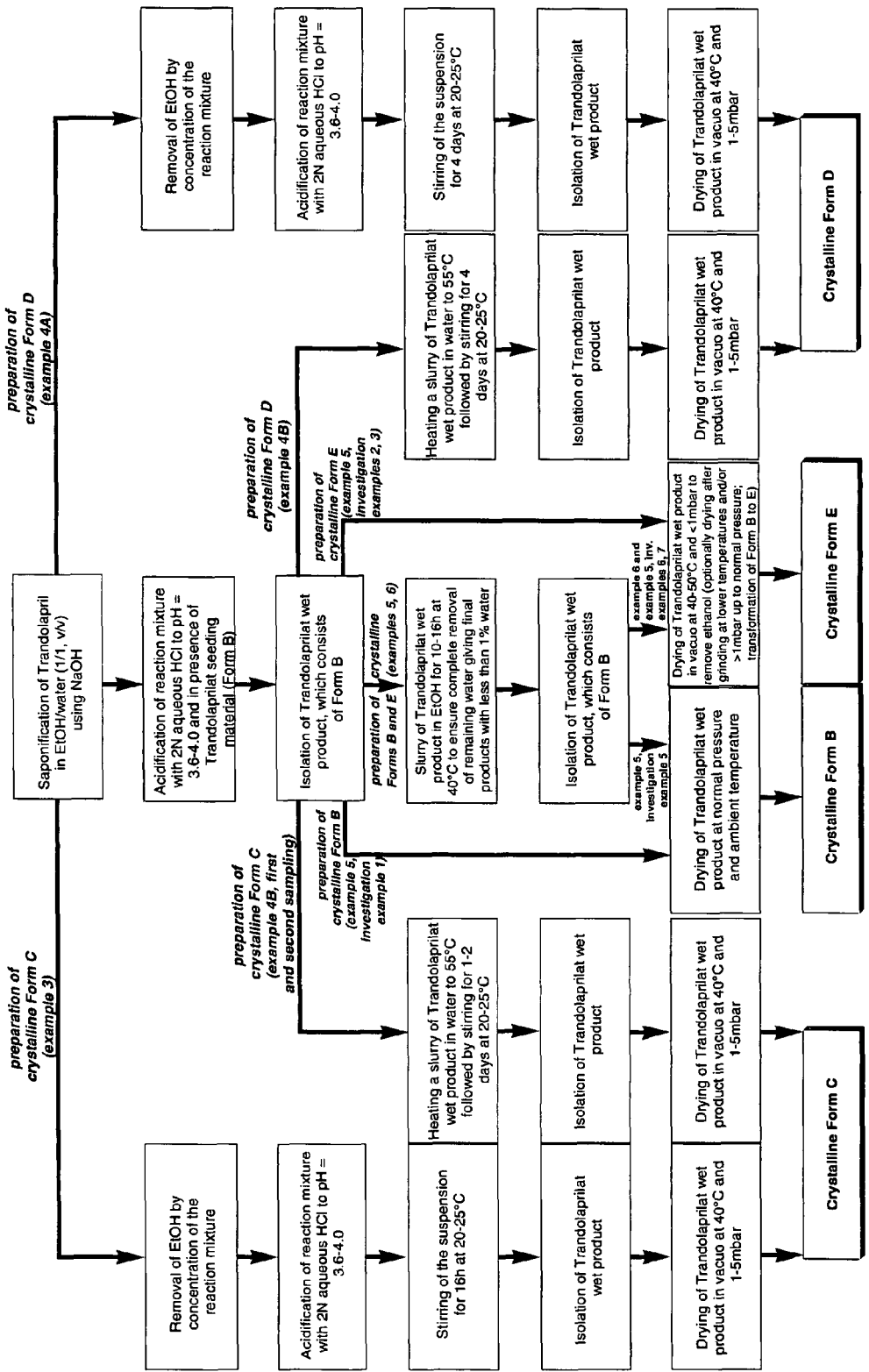
FIG. 17 is an overview showing the method for preparing Trandolaprilat crystalline Forms B to E.

A sample of the third wet product was ground and filled into a PXRD sample holder. The transformation of the pure Trandolaprilat crystalline Form B to Form E at room temperature and normal pressure was followed by successive PXRD measurements (see FIG. 15). The first eighteen measurements were done within 19 hours. The 19th measurement was done after additional storage for 35 hours under the same conditions (the sample was mixed and filled again into the sample holder before the final measurement was carried out).

EXAMPLE 6

Scale Up Procedure for The Preparation of Crystalline Trandolaprilat Form E

Crystalline Trandolaprilat Form E was prepared in the manner described below.

A solution of NaOH (144.8 g, 3.42 mol; assay=94.5%), water (2573 ml), ethanol (2187 ml) and Trandolapril (680 g, 1.58 mol; assay=99.81%) was stirred at an internal temperature ranging from about 20° C. to about 25° C. for 18 hours. After an in process control showed an almost complete saponification (by HPLC), the pH of the clear solution was adjusted to 3.8 by addition of 2N aqueous hydrochloric acid at a temperature ranging from about 20° C. to about 25° C. (The solution was seeded according to the general seeding procedure, see Example 2). The suspension was stirred at a temperature ranging from about 20 to about 25° C. for 5.5 hours, and then filtered off, and the wet product was washed with water (2149 ml) and ethanol (2198 ml). Then, a suspension of the wet product in ethanol (6046 ml) was stirred at a temperature ranging from about 38° C. to about 43° C. for 14 hours, and then at a temperature ranging from about 20° C. to about 25° C. for 2 hours. After filtration, the wet product was washed with ethanol (2224 ml) and dried in vacuo (<1 mbar) at 40° C. until the ethanol content was <0.5% (4 days) to give Trandolaprilat as crystalline Form E (yield: 582 g, 1.44 mol, 91.3%; assay (NaOH)=99.74%; HPLC purity: 99.33%, Trandolaprilat diketopiperazine: 0.52%; water content: 0.54%, ethanol content: 955 ppm, chloride content=not detected).

While the present invention has been described herein with specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the invention be limited only by the scope of the claims which follow, and that such claims be interpreted as broadly as is reasonable.

Throughout this document, various books, patents, journal articles, web sites and other publications have been cited. The entireties of each of these books, patents, journal articles, web sites and other publications are hereby incorporated by reference herein.

What is claimed is:

1. A pseudopolymorphic form of Trandolaprilat comprising crystalline Trandolaprilat Form A having X-ray powder diffraction peaks obtained at degrees two-theta on a copper K alpha scale of 7.7, 9.2, 15.6, 16.4, 18.6, 18.9, 19.8, 20.6, 22.0 and 22.2, wherein one or more of the peaks may have a variation of about +/−0.20 degrees two-theta.

2. The pseudopolymorphic form of Trandolaprilat of claim 1 that has X-ray powder diffraction data obtained at degrees two-theta on a copper K alpha scale as are shown in Table 1, wherein one or more of the peaks may have a variation of about +/−0.20 degrees two-theta, and X-ray powder diffraction peaks obtained on a copper K alpha scale as are shown in FIG. 1:

TABLE 1

| Pos. [°2 Th.] | Height [cts] | d-spacing [Å] | Rel. Int. [%] |
| --- | --- | --- | --- |
| 7.7 | 15534 | 11.5 | 100.0 |
| 9.2 | 2211 | 9.6 | 14.2 |
| 11.4 | 325 | 7.7 | 2.1 |
| 13.2 | 913 | 6.7 | 5.9 |
| 13.5 | 421 | 6.6 | 2.7 |
| 14.3 | 84 | 6.2 | 0.5 |
| 15.6 | 1898 | 5.7 | 12.2 |
| 15.9 | 1087 | 5.6 | 7.0 |
| 16.4 | 1891 | 5.4 | 12.2 |
| 16.9 | 1068 | 5.3 | 6.9 |
| 17.3 | 1246 | 5.1 | 8.0 |
| 17.7 | 1481 | 5.0 | 9.5 |
| 18.2 | 503 | 4.9 | 3.2 |
| 18.6 | 4220 | 4.8 | 27.2 |
| 18.9 | 4715 | 4.7 | 30.4 |
| 19.8 | 3656 | 4.5 | 23.5 |
| 20.6 | 4538 | 4.3 | 29.2 |
| 21.2 | 1141 | 4.2 | 7.3 |
| 22.0 | 5420 | 4.0 | 34.9 |
| 22.2 | 2072 | 4.0 | 13.3 |
| 23.3 | 1242 | 3.8 | 8.0 |
| 23.7 | 731 | 3.8 | 4.7 |
| 23.9 | 491 | 3.7 | 3.2 |
| 24.6 | 1117 | 3.6 | 7.2 |

TABLE 1-continued

| Pos. [°2 Th.] | Height [cts] | d-spacing [Å] | Rel. Int. [%] |
| --- | --- | --- | --- |
| 25.2 | 997 | 3.5 | 6.4 |
| 25.7 | 1055 | 3.5 | 6.8 |
| 26.7 | 1383 | 3.3 | 8.9 |
| 27.0 | 1773 | 3.3 | 11.4 |
| 27.5 | 663 | 3.2 | 4.3 |
| 28.6 | 645 | 3.1 | 4.2 |
| 29.0 | 667 | 3.1 | 4.3 |
| 29.5 | 264 | 3.0 | 1.7 |
| 30.0 | 152 | 3.0 | 0.9 |
| 30.5 | 828 | 2.9 | 5.3 |
| 30.9 | 576 | 2.9 | 3.7 |
| 31.6 | 707 | 2.8 | 4.6 |
| 32.0 | 796 | 2.8 | 5.1 |
| 32.7 | 893 | 2.8 | 5.8 |
| 33.0 | 597 | 2.7 | 3.8 |
| 33.7 | 1154 | 2.6 | 7.4 |
| 34.1 | 250 | 2.6 | 1.6 |
| 34.4 | 251 | 2.6 | 1.6 |
| 35.1 | 748 | 2.6 | 4.8 |
| 35.9 | 881 | 2.5 | 5.7 |
| 36.2 | 576 | 2.5 | 3.7 |
| 38.3 | 355 | 2.4 | 2.3 |
| 38.7 | 316 | 2.3 | 2.0 |
| 39.4 | 140 | 2.3 | 0.9 |

3. The pseudopolymorphic form of Trandolaprilat of claim 1 that is substantially pure.

4. A pseudopolymorphic form of Trandolaprilat comprising crystalline Trandolaprilat Form B having X-ray powder diffraction peaks obtained at degrees two-theta on a copper K alpha scale of 8.1, 9.6, 13.8, 17.4, 18.1, 18.4, 19.3, 20.5, 22.9 and 26.5, wherein one or more of the peaks may have a variation of about +/−0.20 degrees two-theta.

Figure 13:
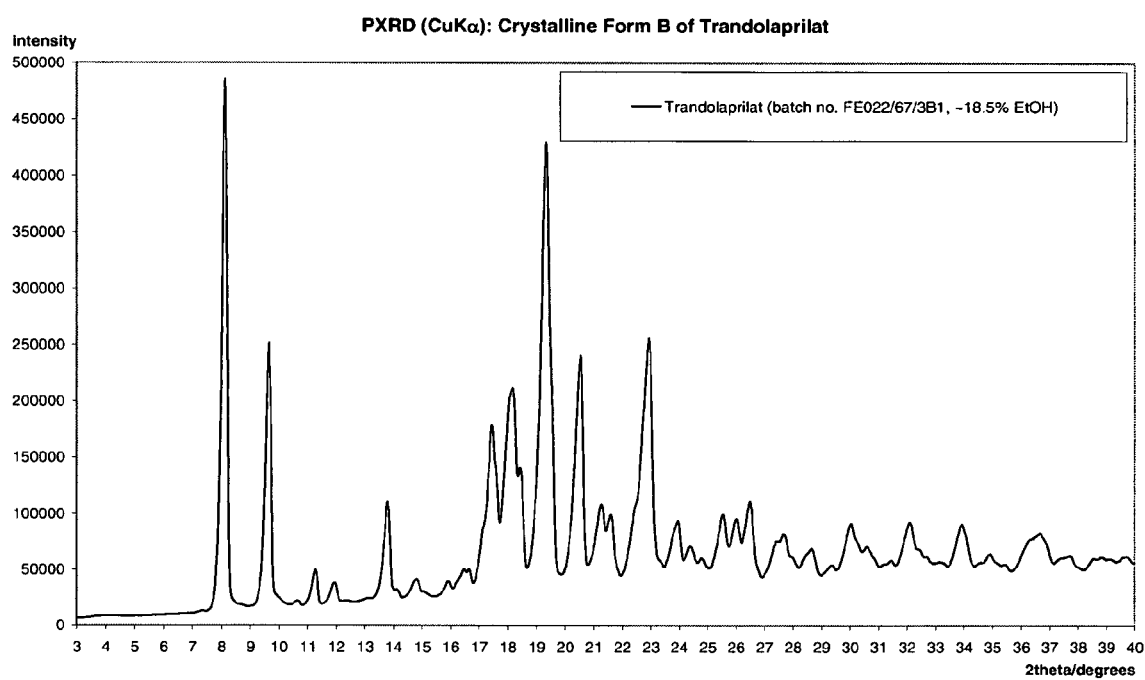
FIG. 13 is an X-ray powder diffraction pattern of crystalline Trandolaprilat Form B
Figure 14:
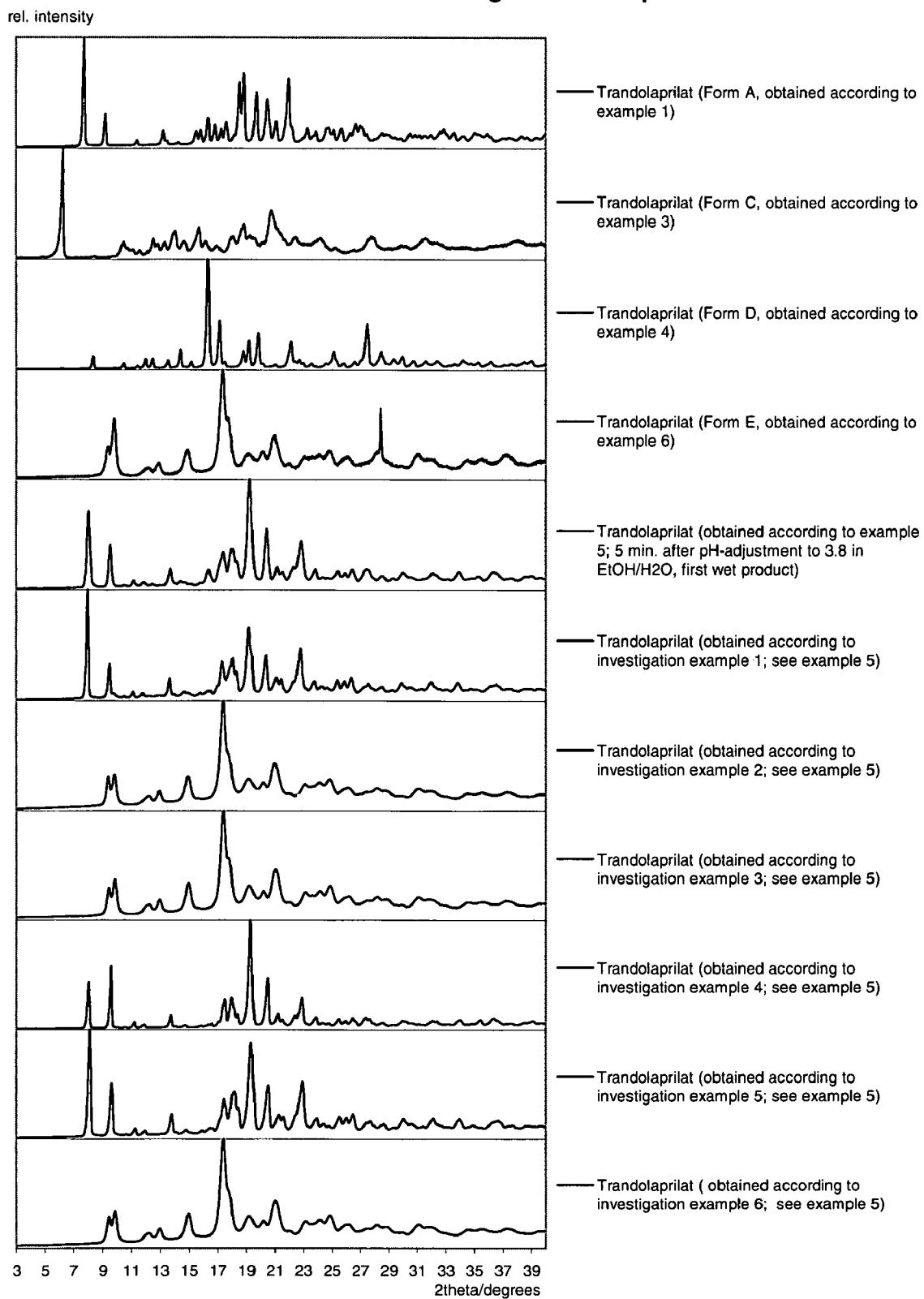
FIG. 14 is an overview of X-ray powder diffraction profiles of the various crystalline Trandolaprilat Forms obtained according to the Examples 1 to 6.

5. The pseudopolymorphic form of Trandolaprilat of claim 4 that has X-ray powder diffraction peaks obtained on a copper K alpha scale that are shown in FIG. 13.

6. The pseudopolymorphic form of Trandolaprilat of claim 4 that has the following X-ray powder diffraction peaks at degrees two-theta obtained on a copper K alpha scale: 8.1, 9.6, 10.6, 11.3, 11.9, 13.8, 14.8, 15.9, 16.6, 17.4, 18.1, 18.4, 19.3, 20.5, 21.2, 21.6, 22.4, 22.9, 23.9, 24.4, 24.8, 25.5, 26.0, 26.5, 27.5, 27.7, 28.6, 29.4, 30.0, 30.6, 32.1, 33.9, 34.9, 36.3, 36.7, 37.7, 38.6 and 39.7, wherein one or more of the peaks may have a variation of about +/−0.20 degrees two-theta.

7. The pseudopolymorphic form of Trandolaprilat of claim 4 that is substantially pure.

8. A pseudopolymorphic form of Trandolaprilat comprising crystalline Trandolaprilat Form C having X-ray powder diffraction peaks obtained at degrees two-theta on a copper K alpha scale of 6.2, 10.4, 12.5, 14.0, 15.7, 18.0, 18.8, 19.3, 20.8 and 27.9, wherein one or more of the peaks may have a variation of about +/−0.20 degrees two-heta.

Figure 8:
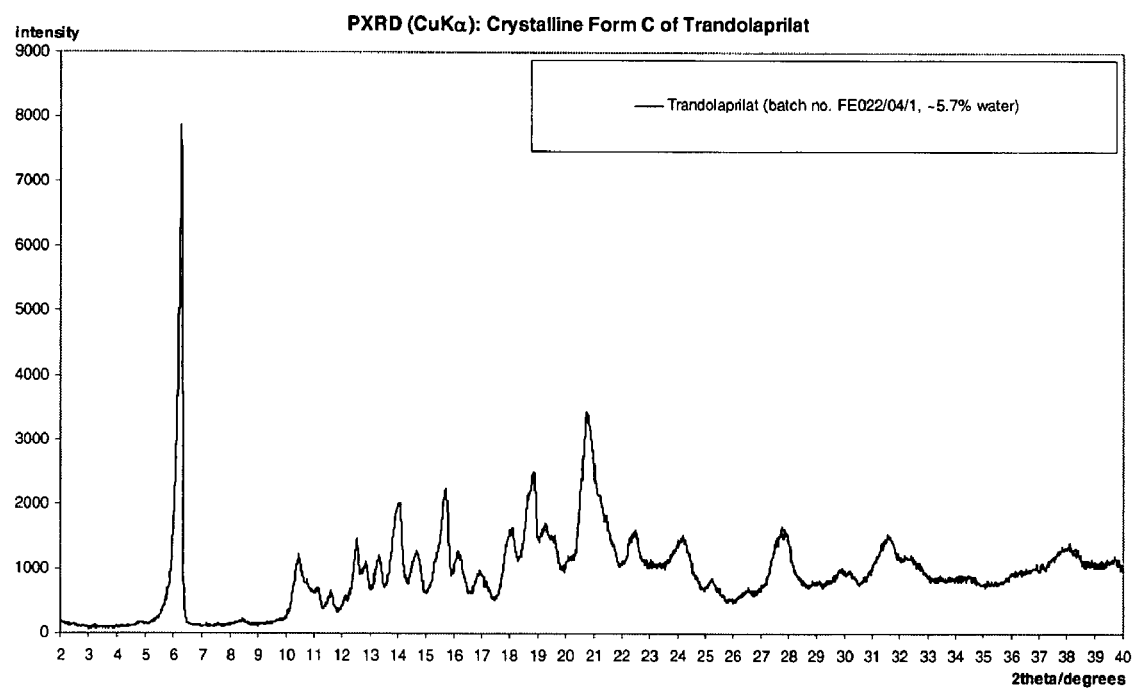
FIG. 8 is an X-ray powder diffraction pattern of crystalline Trandolaprilat Form C.

9. The pseudopolymorphic form of Trandolaprilat of claim 8 that has X-ray powder diffraction data obtained at degrees two-theta on a copper K alpha scale as are shown in Table 4, wherein one or more of the peaks may have a variation of about +/−0.20 degrees two-theta, and X-ray powder diffraction peaks obtained on a copper K alpha scale as are shown in FIG. 8:

TABLE 4

| Pos. [°2 Th.] | Height [cts] | d-spacing [Å] | Rel. Int. [%] |
| --- | --- | --- | --- |
| 4.8 | 68 | 18.2 | 0.9 |
| 6.2 | 7234 | 14.2 | 100.0 |
| 8.4 | 88 | 10.5 | 1.2 |
| 10.4 | 911 | 8.5 | 12.6 |

TABLE 4-continued

| Pos. [°2 Th.] | Height [cts] | d-spacing [Å] | Rel. Int. [%] |
|---|---|---|---|
| 11.1 | 368 | 8.0 | 5.1 |
| 11.6 | 247 | 7.6 | 3.4 |
| 12.1 | 128 | 7.3 | 1.8 |
| 12.5 | 1025 | 7.1 | 14.2 |
| 12.8 | 611 | 6.9 | 8.5 |
| 13.3 | 664 | 6.7 | 9.2 |
| 14.0 | 1452 | 6.3 | 20.1 |
| 14.6 | 550 | 6.1 | 7.6 |
| 15.7 | 1664 | 5.7 | 23.0 |
| 16.2 | 636 | 5.5 | 8.8 |
| 16.9 | 393 | 5.2 | 5.4 |
| 18.0 | 899 | 4.9 | 12.4 |
| 18.8 | 1700 | 4.7 | 23.5 |
| 19.3 | 830 | 4.6 | 11.5 |
| 19.5 | 581 | 4.5 | 8.0 |
| 20.1 | 203 | 4.4 | 2.8 |
| 20.8 | 2400 | 4.3 | 33.2 |
| 21.7 | 366 | 4.1 | 5.1 |
| 22.5 | 601 | 4.0 | 8.3 |
| 24.2 | 731 | 3.7 | 10.1 |
| 25.3 | 236 | 3.5 | 3.3 |
| 26.5 | 129 | 3.4 | 1.8 |
| 27.5 | 733 | 3.2 | 10.1 |
| 27.9 | 904 | 3.2 | 12.5 |
| 29.9 | 223 | 3.0 | 3.1 |
| 30.2 | 211 | 3.0 | 2.9 |
| 31.6 | 718 | 2.8 | 9.8 |
| 32.3 | 338 | 2.8 | 4.7 |
| 36.1 | 93 | 2.5 | 1.3 |
| 38.3 | 264 | 2.4 | 3.7 |

10. The pseudopolymorphic form of Trandolaprilat of claim 8 that is substantially pure.

11. A pseudopolymorphic form of Trandolaprilat comprising crystalline Trandolaprilat Form D having X-ray powder diffraction peaks obtained at degrees two-theta on a copper K alpha scale of 14.4, 16.4, 17.2, 18.8, 19.2, 19.9, 22.2, 25.2, 27.5 and 28.5, wherein one or more of the peaks may have a variation of about +/−0.20 degrees two-theta.

Figure 9:
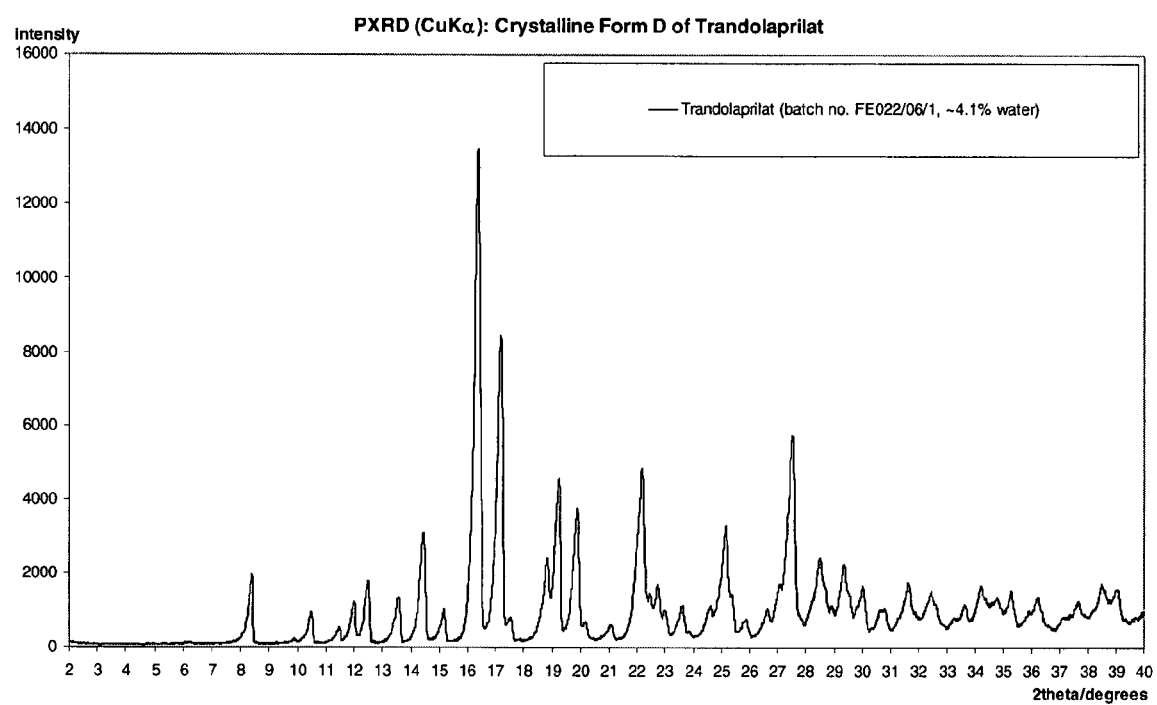
FIG. 9 is an X-ray powder diffraction pattern of crystalline Trandolaprilat Form D.
Figure 10:
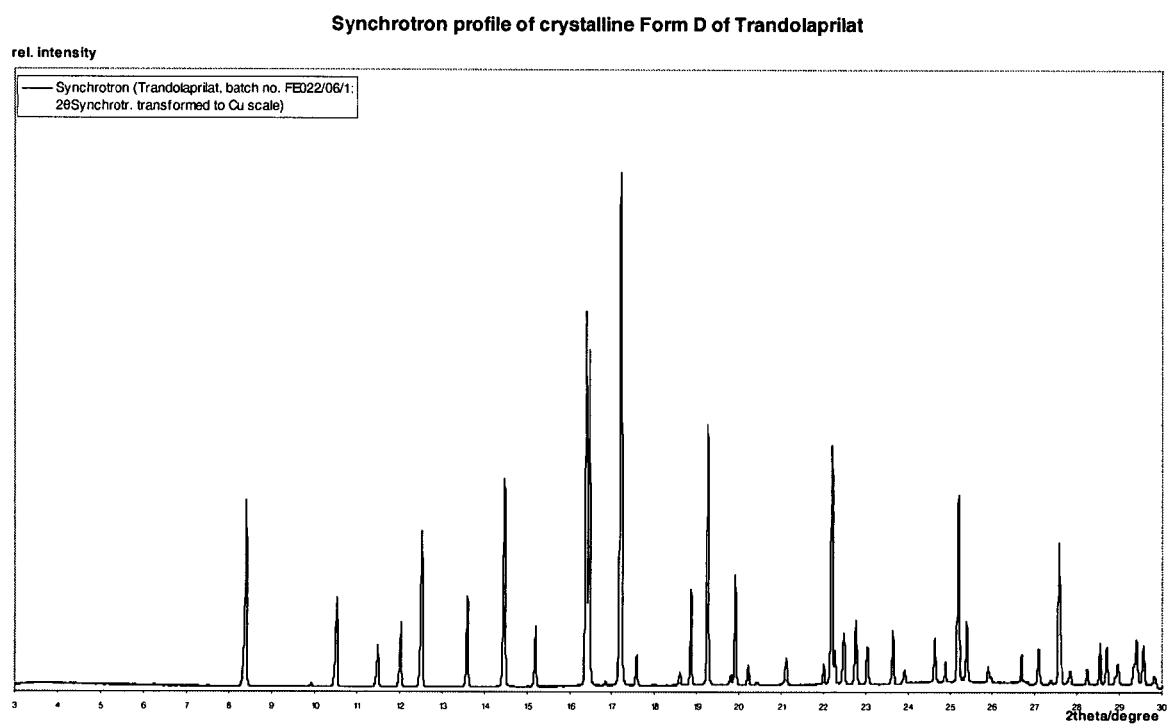
FIG. 10 is a graph that shows the synchrotron profile of crystalline Trandolaprilat Form D.

12. The pseudopolymorphic form of Trandolaprilat of claim 11 that has X-ray powder diffraction data obtained at degrees two-theta on a copper K alpha scale as are shown in Table 5, wherein one or more of the peaks may have a variation of about +/−0.20 degrees two-theta, and X-ray powder diffraction peaks obtained on a copper K alpha scale as are shown in FIG. 9:

TABLE 5

| Pos. [°2 Th.] | Height [cts] | d-spacing [Å] | Rel. Int. [%] |
|---|---|---|---|
| 6.2 | 50 | 4.3 | 0.4 |
| 8.4 | 1899 | 10.6 | 14.3 |
| 10.5 | 874 | 8.4 | 6.6 |
| 11.5 | 461 | 7.7 | 3.5 |
| 12.0 | 1183 | 7.4 | 8.9 |
| 12.5 | 1748 | 7.1 | 13.2 |
| 13.6 | 1252 | 6.5 | 9.5 |
| 14.4 | 3036 | 6.1 | 22.9 |
| 15.2 | 969 | 5.8 | 7.3 |
| 16.4 | 13246 | 5.4 | 100.0 |
| 17.2 | 8374 | 5.2 | 63.2 |
| 17.5 | 710 | 5.1 | 5.4 |
| 18.8 | 2385 | 4.7 | 18.0 |
| 19.2 | 4452 | 4.6 | 33.6 |
| 19.9 | 3709 | 4.5 | 28.0 |
| 20.2 | 634 | 4.4 | 4.8 |
| 21.1 | 549 | 4.2 | 4.1 |
| 22.2 | 4817 | 4.0 | 36.4 |
| 22.5 | 1818 | 4.0 | 13.7 |
| 22.7 | 1501 | 3.9 | 11.3 |
| 23.0 | 933 | 3.9 | 7.1 |
| 23.6 | 1001 | 3.8 | 7.6 |

TABLE 5-continued

| Pos. [°2 Th.] | Height [cts] | d-spacing [Å] | Rel. Int. [%] |
|---|---|---|---|
| 23.9 | 367 | 3.7 | 2.8 |
| 24.6 | 1037 | 3.6 | 7.8 |
| 25.2 | 3240 | 3.5 | 24.5 |
| 25.8 | 659 | 3.5 | 5.0 |
| 26.6 | 948 | 3.4 | 7.2 |
| 27.1 | 1656 | 3.3 | 12.5 |
| 27.5 | 5696 | 3.2 | 43.0 |
| 28.5 | 2383 | 3.1 | 18.0 |
| 29.4 | 2130 | 3.0 | 16.1 |
| 30.0 | 1600 | 3.0 | 12.1 |
| 30.8 | 995 | 2.9 | 7.5 |
| 31.7 | 1694 | 2.8 | 12.8 |
| 32.5 | 1471 | 2.8 | 11.1 |
| 33.3 | 714 | 2.7 | 5.4 |
| 33.7 | 1102 | 2.7 | 8.3 |
| 34.2 | 1568 | 2.6 | 11.8 |
| 34.8 | 1262 | 2.6 | 9.5 |
| 35.3 | 1447 | 2.5 | 10.9 |
| 36.2 | 1249 | 2.5 | 9.4 |
| 37.7 | 1121 | 2.4 | 8.5 |
| 38.5 | 1619 | 2.3 | 12.2 |
| 39.0 | 1491 | 2.3 | 11.3 |

13. The pseudopolymorphic form of Trandolaprilat of claim 11 that is substantially pure.

14. A polymorphic form of Trandolaprilat comprising crystalline Trandolaprilat Form E having X-ray powder diffraction peaks obtained at degrees two-theta on a copper K alpha scale of 9.4, 9.8, 14.9, 17.4, 17.7, 19.2, 20.2, 21.0, 24.8 and 28.4, wherein one or more of the peaks may have a variation of about +/−0.20 degrees two-theta.

Figure 11:
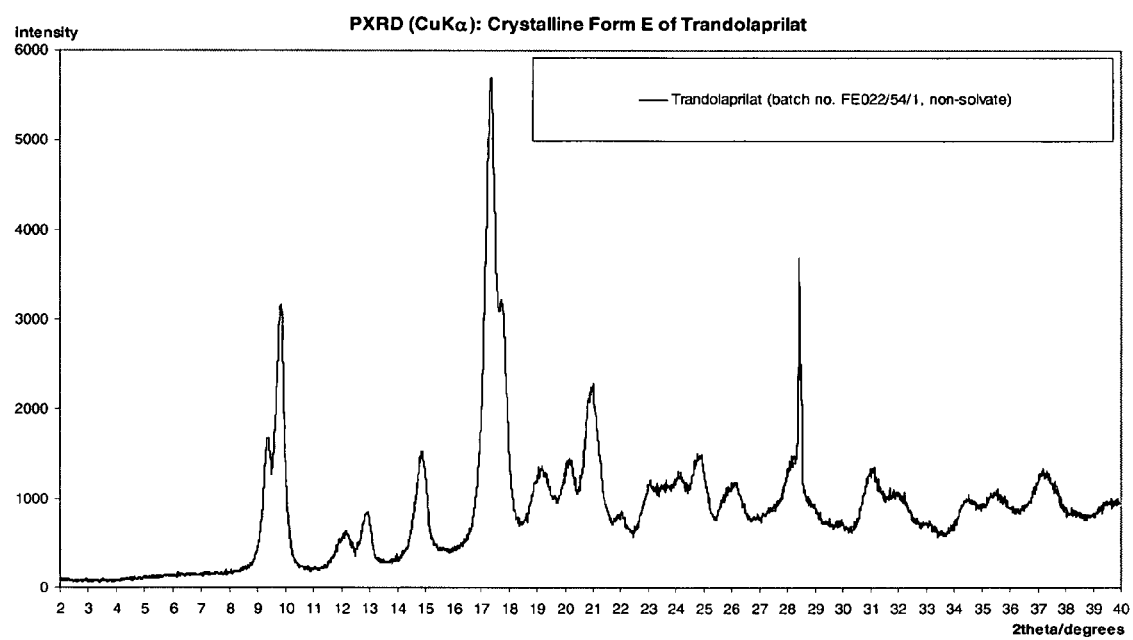
FIG. 11 is an X-ray powder diffraction pattern of crystalline Trandolaprilat Form E (containing Si as a standard).

15. The polymorphic form of Trandolaprilat of claim 14 that has X-ray powder diffraction data obtained at degrees two-theta on a copper K alpha scale as are shown in Table 8, wherein one or more of the peaks may have a variation of about +/−0.20 degrees two-theta, and X-ray powder diffraction peaks obtained on a copper K alpha scale as are shown in FIG. 11:

TABLE 8

| Pos. [°2 Th.] | Height [cts] | d-spacing [Å] | Rel. Int. [%] |
|---|---|---|---|
| 9.4 | 1501 | 9.4 | 27.9 |
| 9.8 | 2865 | 9.0 | 53.3 |
| 12.2 | 393 | 7.3 | 7.3 |
| 12.9 | 592 | 6.9 | 11.0 |
| 14.9 | 1214 | 6.0 | 22.6 |
| 17.4 | 5380 | 5.1 | 100.0 |
| 17.7 | 2818 | 5.0 | 52.4 |
| 19.2 | 963 | 4.6 | 17.9 |
| 20.2 | 1049 | 4.4 | 19.5 |
| 21.0 | 1838 | 4.2 | 34.2 |
| 22.1 | 403 | 4.0 | 7.5 |
| 23.1 | 759 | 3.9 | 14.1 |
| 24.8 | 998 | 3.6 | 18.6 |
| 26.1 | 679 | 3.4 | 12.6 |
| 28.4 | 2449 | 3.1 | 45.5 |
| 31.1 | 757 | 2.9 | 14.1 |
| 31.9 | 463 | 2.8 | 8.6 |
| 34.5 | 325 | 2.6 | 6.0 |
| 35.5 | 361 | 2.5 | 6.7 |
| 37.2 | 539 | 2.4 | 10.0 |

16. The polymorphic form of Trandolaprilat of claim 14 that is substantially pure.

17. The polymorphic form of Trandolaprilat of claim 14 wherein the Trandolaprilat does not contain an amount of water that exceeds about 1%.

18. The polymorphic form of Trandolaprilat of claim 14 wherein the Trandolaprilat does not contain a combined amount of one or more residual solvents that exceeds limits that are currently acceptable for pharmaceuticals.

19. A pharmaceutical composition comprising a therapeutically effective amount of at least one Trandolaprilat compound and a pharmaceutically acceptable carrier, wherein the Trandolaprilat compound is crystalline Trandolaprilat Form A having X-ray powder diffraction peaks obtained at degrees two-theta on a copper K alpha scale of 7.7, 9.2, 15.6, 16.4, 18.6, 18.9, 19.8, 20.6, 22.0 and 22.2, crystalline Trandolaprilat Form B having X-ray powder diffraction peaks obtained at degrees two-theta on a copper K alpha scale of 8.1, 9.6, 13.8, 17.4, 18.1, 18.4, 19.3, 20.5, 22.9 and 26.5, crystalline Trandolaprilat Form C having X-ray powder diffraction peaks obtained at degrees two-theta on a copper K alpha scale of 6.2, 10.4, 12.5, 14.0, 15.7, 18.0, 18.8, 19.3, 20.8 and 27.9, crystalline Trandolaprilat Form D having X-ray powder diffraction peaks obtained at degrees two-theta on a copper K alpha scale of 14.4, 16.4, 17.2, 18.8, 19.2, 19.9, 22.2, 25.2, 27.5 and 28.5, crystalline Trandolaprilat Form E having X-ray powder diffraction peaks obtained at degrees two-theta on a copper K alpha scale of 9.4, 9.8, 14.9, 17.4, 17.7, 19.2, 20.2, 21.0, 24.8 and 28.4, or any combination thereof, wherein one or more of the peaks may have a variation of about +/−0.20 degrees two-theta, and wherein the Trandolaprilat compound is present in a crystalline form.

20. The pharmaceutical composition of claim 19 wherein the pharmaceutical composition is in an oral dosage form or that may be administered transdermally.

21. The pharmaceutical composition of claim 20 wherein the pharmaceutical composition is in a form of a tablet or capsule or in a form of a transdermal patch.

22. A method for treating high blood pressure or cardiac insufficiency comprising administering to a subject in need of such treatment an effective amount of a pharmaceutical composition of claim 19.

23. Crystalline Trandolaprilat Form A having the following X-ray powder diffraction peaks at degrees two-theta obtained on a copper K alpha scale: 7.7, 9.2, 11.4, 13.2, 13.5, 14.3, 15.6, 15.9, 16.4, 16.9, 17.3, 17.7, 18.2, 18.6, 18.9, 19.8, 20.6, 21.2, 22.0, 22.2, 23.3, 23.7, 23.9, 24.6, 25.2, 25.7, 26.7, 27.0, 27.5, 28.6, 29.0, 29.5, 30.0, 30.5, 30.9, 31.6, 32.0, 32.7, 33.0, 33.7, 34.1, 34.4, 35.1, 35.9, 36.2, 38.3, 38.7 and 39.4, wherein one or more of the peaks may have a variation of about +/−0.20 degrees two-theta.

24. Crystalline Trandolaprilat Form A according to claim 1 having X-ray powder diffraction peaks obtained on a copper K alpha scale as are shown in FIG. 1.

25. Crystalline Trandolaprilat Form A according to claim 2 that is substantially pure.

26. Crystalline Trandolaprilat Form B having the following X-ray powder diffraction peaks at degrees two-theta obtained on a copper K alpha scale: 8.1, 9.6, 10.6, 11.3, 11.9, 13.8, 14.8, 15.9, 16.6, 17.4, 18.1, 18.4, 19.3, 20.5, 21.2, 21.6, 22.4, 22.9, 23.9, 24.4, 24.8, 25.5, 26.0, 26.5, 27.5, 27.7, 28.6, 29.4, 30.0, 30.6, 32.1, 33.9, 34.9, 36.3, 36.7, 37.7, 38.6 and 39.7, wherein one or more of the peaks may have a variation of about +/−0.20 degrees two-theta.

27. Crystalline Trandolaprilat Form B according to claim 4 having X-ray powder diffraction data at degrees two-theta obtained on a copper K alpha scale as are shown in Table 10, wherein one or more of the peaks may have a variation of about +/−0.20 degrees two-theta, and X-ray powder diffraction peaks obtained on a copper K alpha scale as are shown in FIG. 13:

TABLE 10

| Pos. [°2 Th.] | Height [cts] | d-spacing [Å] | Rel. Int. [%] |
|---|---|---|---|
| 8.1 | 485321 | 10.9 | 100 |
| 9.6 | 251491 | 9.2 | 51.8 |
| 10.6 | 22079 | 8.3 | 4.5 |
| 11.3 | 49787 | 7.9 | 10.3 |
| 11.9 | 38231 | 7.4 | 7.9 |
| 13.8 | 110823 | 6.4 | 22.8 |
| 14.8 | 41587 | 6.0 | 8.6 |
| 15.9 | 39706 | 5.6 | 8.2 |
| 16.6 | 50332 | 5.3 | 10.4 |
| 17.4 | 178820 | 5.1 | 36.8 |
| 18.1 | 211405 | 4.9 | 43.6 |
| 18.4 | 140642 | 4.8 | 29.0 |
| 19.3 | 430165 | 4.6 | 88.6 |
| 20.5 | 241048 | 4.3 | 49.7 |
| 21.2 | 108775 | 4.2 | 22.4 |
| 21.6 | 99472 | 4.1 | 20.5 |
| 22.4 | 103529 | 4.0 | 21.3 |
| 22.9 | 256485 | 3.9 | 52.8 |
| 23.9 | 94042 | 3.7 | 19.4 |
| 24.4 | 70724 | 3.6 | 14.6 |
| 24.8 | 60099 | 3.6 | 12.4 |
| 25.5 | 99950 | 3.5 | 20.6 |
| 26.0 | 95754 | 3.4 | 19.7 |
| 26.5 | 111361 | 3.4 | 22.9 |
| 27.5 | 75690 | 3.3 | 15.6 |
| 27.7 | 81574 | 3.2 | 16.8 |
| 28.6 | 68696 | 3.1 | 14.2 |
| 29.4 | 53969 | 3.0 | 11.1 |
| 30.0 | 91367 | 3.0 | 18.8 |
| 30.6 | 70719 | 2.9 | 14.6 |
| 32.1 | 92500 | 2.8 | 19.1 |
| 33.9 | 90615 | 2.6 | 18.7 |
| 34.9 | 63904 | 2.6 | 13.2 |
| 36.3 | 77597 | 2.5 | 16.0 |
| 36.7 | 83061 | 2.5 | 17.1 |
| 37.7 | 62646 | 2.4 | 12.9 |
| 38.6 | 60200 | 2.3 | 12.4 |
| 39.7 | 61743 | 2.3 | 12.7 |

28. Crystalline Trandolaprilat Form B according to claim 5 that is substantially pure.

29. Crystalline Trandolaprilat Form C having the following X-ray powder diffraction peaks at degrees two-theta obtained on a copper K alpha scale: 4.8, 6.2, 8.4, 10.4, 11.1, 11.6, 12.1, 12.5, 12.8, 13.3, 14.0, 14.6, 15.7, 16.2, 16.9, 18.0, 18.8, 19.3, 19.5, 20.1, 20.8, 21.7, 22.5, 24.2, 25.3, 26.5, 27.5, 27.9, 29.9, 30.2, 31.6, 32.3, 36.1 and 38.3, wherein one or more of the peaks may have a variation of about +/−0.20 degrees two-theta.

30. Crystalline Trandolaprilat Form C according to claim 8 having X-ray powder diffraction peaks obtained on a copper K alpha scale as are shown in FIG. 8.

31. Crystalline Trandolaprilat Form C according to claim 9 that is substantially pure.

32. Crystalline Trandolaprilat Form D having the following X-ray powder diffraction peaks at degrees two-theta obtained on a copper K alpha scale: 6.2, 8.4, 10.5, 11.5, 12.0, 12.5, 13.6, 14.4, 15.2, 16.4, 17.2, 17.5, 18.8, 19.2, 19.9, 20.2, 21.1, 22.2, 22.5, 22.7, 23.0, 23.6, 23.9, 24.6, 25.2, 25.8, 26.6, 27.1, 27.5, 28.5, 29.4, 30.0, 30.8, 31.7, 32.5, 33.3, 33.7, 34.2, 34.8, 35.3, 36.2, 37.7, 38.5 and 39.0, wherein one or more of the peaks may have a variation of about +/−0.20 degrees two-theta.

33. Crystalline Trandolaprilat Form D according to claim 11 having X-ray powder diffraction peaks obtained on a copper K alpha scale as are shown in FIG. 9.

34. Crystalline Trandolaprilat Form D according to claim 12 that is substantially pure.

35. Crystalline Trandolaprilat Form E having the following X-ray powder diffraction peaks at degrees two-theta obtained on a copper K alpha scale: 9.4, 9.8, 12.2, 12.9, 14.9, 17.4, 17.7, 19.2, 20.2, 21.0, 22.1, 23.1, 24.8, 26.1, 28.4, 31.1, 31.9, 34.5, 35.5 and 37.2, wherein one or more of the peaks may have a variation of about +/−0.20 degrees two-theta.

36. Crystalline Trandolaprilat Form E according to claim 14 having X-ray powder diffraction peaks obtained on a copper K alpha scale as are shown in FIG. 11.

37. Crystalline Trandolaprilat Form E according to claim 15 that is substantially pure.

38. Crystalline Trandolaprilat Form E according to claim 14 having a water content that is about 1% or less.

39. Crystalline Trandolaprilat Form E according to claim 14 having an amount of residual solvent that is 1% or less.

40. A pharmaceutical composition comprising at least one crystalline Trandolaprilat selected from the group consisting of: (1) Trandolaprilat Form A having the following X-ray powder diffraction peaks at degrees two-theta obtained on a copper K alpha scale: 7.7, 9.2, 11.4, 13.2, 13.5, 14.3, 15.6, 15.9, 16.4, 16.9, 17.3, 17.7, 18.2, 18.6, 18.9, 19.8, 20.6, 21.2, 22.0, 22.2, 23.3, 23.7, 23.9, 24.6, 25.2, 25.7, 26.7, 27.0, 27.5, 28.6, 29.0, 29.5, 30.0, 30.5, 30.9, 31.6, 32.0, 32.7, 33.0, 33.7, 34.1, 34.4, 35.1, 35.9, 36.2, 38.3, 38.7 and 39.4; (2) Trandolaprilat Form B having the following X-ray powder diffraction peaks at degrees two-theta obtained on a copper K alpha scale: 8.1, 9.6, 10.6, 11.3, 11.9, 13.8, 14.8, 15.9, 16.6, 17.4, 18.1, 18.4, 19.3, 20.5, 21.2, 21.6, 22.4, 22.9, 23.9, 24.4, 24.8, 25.5, 26.0, 26.5, 27.5, 27.7, 28.6, 29.4, 30.0, 30.6, 32.1, 33.9, 34.9, 36.3, 36.7, 37.7, 38.6 and 39.7; (3) Trandolaprilat Form C having the following X-ray powder diffraction peaks at degrees two-theta obtained on a copper K alpha scale: 4.8, 6.2, 8.4, 10.4, 11.1, 11.6, 12.1, 12.5, 12.8, 13.3, 14.0, 14.6, 15.7, 16.2, 16.9, 18.0, 18.8, 19.3, 19.5, 20.1, 20.8, 21.7, 22.5, 24.2, 25.3, 26.5, 27.5, 27.9, 29.9, 30.2, 31.6, 32.3, 36.1 and 38.3; (4) Trandolaprilat Form D having the following X-ray powder diffraction peaks at degrees two-theta obtained on a copper K alpha scale: 6.2, 8.4, 10.5, 11.5, 12.0, 12.5, 13.6, 14.4, 15.2, 16.4, 17.2, 17.5, 18.8, 19.2, 19.9, 20.2, 21.1, 22.2, 22.5, 22.7, 23.0, 23.6, 23.9, 24.6, 25.2, 25.8, 26.6, 27.1, 27.5, 28.5, 29.4, 30.0, 30.8, 31.7, 32.5, 33.3, 33.7, 34.2, 34.8, 35.3, 36.2, 37.7, 38.5 and 39.0; and (5) Trandolaprilat Form E having the following X-ray powder diffraction peaks at degrees two-theta obtained on a copper K alpha scale: 9.4, 9.8, 12.2, 12.9, 14.9, 17.4, 17.7, 19.2, 20.2, 21.0, 22.1, 23.1, 24.8, 26.1, 28.4, 31.1, 31.9, 34.5, 35.5 and 37.2; wherein one or more of the peaks may have a variation of about +/−0.20 degrees two-theta, and wherein the crystalline Trandolaprilat is present in a crystalline form.

41. The pharmaceutical composition of claim 19 wherein the pharmaceutical composition is in a form of a tablet, a capsule or a transdermal patch.

* * * * *